United States Patent
McElwee-White et al.

(10) Patent No.: US 9,540,284 B2
(45) Date of Patent: Jan. 10, 2017

(54) TUNGSTEN NITRIDO PRECURSORS FOR THE CVD OF TUNGSTEN NITRIDE, CARBONITRIDE, AND OXIDE FILMS

(71) Applicant: UNIVERSITY OF FLORIDA RESEARCH FOUNDATION, INC., Gainesville, FL (US)

(72) Inventors: Lisa McElwee-White, Gainesville, FL (US); Timothy James Anderson, Amherst, MA (US); K. Randall McClain, Gainesville, FL (US); Christopher O'Donohue, Conshohocken, PA (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 14/575,026

(22) Filed: Dec. 18, 2014

(65) Prior Publication Data
US 2015/0105234 A1    Apr. 16, 2015

Related U.S. Application Data

(63) Continuation-in-part of application No. PCT/US2013/046390, filed on Jun. 18, 2013.
(Continued)

(51) Int. Cl.
C07F 11/00 (2006.01)
C04B 35/58 (2006.01)
(Continued)

(52) U.S. Cl.
CPC ....... C04B 35/58007 (2013.01); C07F 11/005 (2013.01); C23C 16/30 (2013.01);
(Continued)

(58) Field of Classification Search
CPC .................... C07F 11/005; C04B 35/58007
(Continued)

(56) References Cited

U.S. PATENT DOCUMENTS 6,379,748 B1    4/2002    Bhandari et al.
6,596,888 B2    7/2003    McElwee-White et al.
(Continued)

OTHER PUBLICATIONS

Gebeyehu et al., Chemical Abstracts, Abstract No. 115:173314 (1991) for the article in Zeitschrift fuer Anorganische und Allgemeine Chemie (1991), vol. 593, pp. 99-110.*
(Continued)

*Primary Examiner* — Porfirio Nazario Gonzalez
(74) *Attorney, Agent, or Firm* — Saliwanchik, Lloyd & Eisenschenk

(57) ABSTRACT

Embodiments of the invention are directed to a method of preparing a $WN_x$, $WN_xC_y$, $WN_xO_z$, and $WN_xC_yO_z$ solid by the deposition of a $WN_x$ precursor at a temperature below 300° C. The $WN_x$ precursor is a tungsten nitrido complex. The deposition can be carried out using a tungsten nitrido complex as a single-source metal organic precursor. In an embodiment of the invention, the deposition can be performed to form a plurality of $WN_x$, $WN_xC_y$, $WN_xO_z$, $WN_xC_yO_z$ nanoparticles.

6 Claims, 13 Drawing Sheets

Related U.S. Application Data

(60) Provisional application No. 61/661,171, filed on Jun. 18, 2012.

(51) Int. Cl.
  *C23C 16/30* (2006.01)
  *C23C 16/34* (2006.01)
  *C23C 16/36* (2006.01)

(52) U.S. Cl.
  CPC ............ *C23C 16/308* (2013.01); *C23C 16/34* (2013.01); *C23C 16/36* (2013.01)

(58) Field of Classification Search
  USPC .............................................. 556/57; 501/87
  See application file for complete search history.

(56) References Cited

U.S. PATENT DOCUMENTS

| | | |
|---|---|---|
| 2003/0198587 A1 | 10/2003 | Kaloyeros et al. |
| 2006/0125099 A1 | 6/2006 | Gordon et al. |
| 2007/0160761 A1 | 7/2007 | Reuter et al. |

OTHER PUBLICATIONS

Chiu, H-T. et al., "Tungsten nitride thin films prepared by MOCVD," *J. Mater. Res.*, Jun. 1993, pp. 1353-1360, vol. 8, No. 6.

Greco, J.B., "Synthetic Approaches to New Three Coordinate Group 6 Compounds: Chromium Alkenyls, Molybdenum Thiolates and Tungsten Amides," Ph.D. Dissertation, Submitted to the Department of Chemistry, Massachusetts Institute of Technology (Cambridge, MA), May 2001 (relevant experimental procedure).

Ajmera, H.M. et al., "Deposition of $WN_xC_y$ for diffusion barrier application using the imido guanidinato complex W($N^iPr$)$Cl_3$[$^iPriNC(NMe_2)$ $N^iPr$]," *Journal of Vacuum Science & Technology B*, Sep./Oct. 2008, pp. 1800-1807, vol. 26, No. 5.

Bchir, O.J. et al., "MOCVD of tungsten nitride ($WN_x$) thin films from the imido complex $Cl_4(CH_3CN)W(N^iPr)$," *Journal of Crystal Growth*, pp. 262-274, vol. 249.

Bchir, O.J. et al., "$Cl_4(PhCN)W(NPh)$ as a single-source MOCVD precursor for deposition of tungsten nitride ($WN_x$) thin films," *Journal of Organometallic Chemistry*, 2003, pp. 338-350, vol. 684.

Bchir, O.J. et al., "Tungsten Allylimido Complexes $Cl_4(RCN)W(NC_3H_5)$ as Single-Source CVD Precursors for $WN_xC_y$ Thin Films. Correlation of Precursor Fragmentation to Film Properties," *J. Am. Chem. Soc.*, 2005, pp. 7825-7833, vol. 127.

Becker, J.S. et al., "Diffusion barrier properties of tungsten nitride films grown by atomic layer deposition from bis(*tert*-butylimido)bis(dimethylamido)tungsten and ammonia," *Applied Physics Letters*, Apr. 7, 2003, pp. 2239-2241, vol. 82, No. 14.

Becker, J.S., et al., "Highly Conformal Thin Films of Tungsten Nitride Prepared by Atomic Layer Deposition from a Novel Precursor," *Chem. Mater.*, 2003, pp. 2969-2976, vol. 15.

Burroughs, B.A. et al., "Metathesis of Nitrogen Atoms within Triple Bonds Involving Carbon, Tungsten, and Molybdenum," *Inorg. Chem.*, 2008, pp. 5377-5385, vol. 47.

Chisholm, M.H. etal., "Isoelectronic Molecules with Triple Bonds to Metal Atoms (M=Mo, W): Crystal and Molecular Structures of Tri-*tert*-butoxytungsten Ethylidyne and Nitride," *Inorg. Chem.*, 1983, pp. 2903-2906, vol. 22.

Close, M.R. et al., "Synthesis and Structure of $WNCl_3$ and Evidence for Structural Modifications with Bound Chlorocarbon Solvents," *Inorg. Chem.*, 1994, pp. 4198-4201, vol. 33.

El-Kadri, O.M. et al., "Film growth precursor development for metal nitrides. Synthesis, structure, and volatility of molybdenum(VI) and tungsten(VI) complexes containing bis(imido)metal fragments and various nitrogen donor ligands," *Dalton Trans.*, 2006, pp. 1943-1953.

Gwildies, V. et al., "All-Nitrogen Coordinated Aminato/Imido Complexes of Molybdenum and Tungsten: Syntheses and Characterization," *Inorg. Chem.*, 2010, pp. 8487-8494, vol. 49.

Koller, J. et al., "Synthesis and Characterization of Diorganohydrazido(2−) Tungsten Complexes," *Inorg. Chem.*, 2008, pp. 4457-4462, vol. 47, No. 11.

McClain, K.R. et al., "Synthesis of $WN(NMe_2)_3$ as a Precursor for the Deposition of $Wn_x$ Nanospheres," *Eur. J. Inorg. Chem.* 2012, pp. 4579-4584.

McClain, K.R. et al., "Tunsten Nitrido Complexes as Precursors for Low Temperature Chemical Vapor Deposition of $WN_xC_y$ Films as Diffusion Barriers for Cu Metallization," *J. Am. Chem. Soc.*, 2014, pp. 1650-1662, vol. 136.

McElwee-White, L., "Design of precursors for the CVD of inorganic thin films," *Dalton Trans.*, 2006, pp. 5327-5333.

O'Donohue, C.T. et al., "Low Temperature Deposition of $WN_xC_y$ Diffusion Barriers Using $WN(NEt_2)_3$ as a Single-Source Precursor," *ECS Journal of Solid State Science and Technology*, 2015, pp. N3180-N3187, vol. 4, No. 1.

Potts, S.E. et al., "Tungsten imido complexes as precursors to tungsten carbonitride thin films," *Dalton Trans.*, 2008, pp. 5730-5736.

Rische, D. et al., "Mixed Guanidinato/Alkylimido/Azido Tunsten(VI) Complexes: Synthesis and Structural Characterization," *Inorg. Chem.*, 2006, pp. 269-277, vol. 45.

Rische, D. et al., "Guanidinato-based precursors for MOCVD of metal nitrides ($M_xN$: M=Ta, W)," *Surface & Coatings Technology*, 2007, pp. 9125-9130, vol. 201.

Schrock, R.R. etal., "Metathesis of Tungsten-Tungsten Triple Bonds with Acetylenes and Nitriles to Give Alkylidyne and Nitrido Complexes," *J. Am. Chem. Soc.*, 1982, pp. 4291-4293, vol. 104.

Won, Y.S. et al., "Homogeneous Decomposition of Aryl- and Alkylimido Precursors for the Chemical Vapor Deposition of Tungsten Nitride: A Combined Density Functional Theory and Experimental Study," *J. Am. Chem. Soc.*, 2006, pp. 13781-13788, vol. 128.

* cited by examiner

TUNGSTEN NITRIDO PRECURSORS FOR THE CVD OF TUNGSTEN NITRIDE, CARBONITRIDE, AND OXIDE FILMS

CROSS-REFERENCE TO RELATED APPLICATION

This application is a continuation-in-part of International Patent Application No. PCT/US2013/046390, filed Jun. 18, 2013, which claims the benefit of U.S. Provisional Patent Application Ser. No. 61/661,171, filed Jun. 18, 2012, the disclosures of which are hereby incorporated by reference in their entirety.

This invention was made with government support under CHE-0911640/CHE-1061982 awarded by the National Science Foundation. The government has certain rights in the invention.

BACKGROUND OF INVENTION

In many cases, barrier layers are needed to prevent the diffusion of one material to an adjacent material during the preparation or use. As an example, an integrated circuit (IC) device requires extremely thin barrier layers to prevent interdiffusion. In particular the use of barrier layers has become more important as copper (Cu) has been used in metallization of VLSI microelectronic devices due to its high conductivity and relatively low resistance to electromigration. The Cu is now deposited typically by a physical deposition method but as film thickness is reduced, chemical deposition techniques will required to achieve nm-scale thick layers that are conformal. Chemical vapor deposition (CVD) processes permit large-scale manufacturing and the conformal seeding of high aspect ratio inter-level vias in high density integrated circuits (bulk filled by ECD), but the Cu is quite mobile in silicon. Cu diffuses and reacts rapidly with silicon (Si) to form compounds, such as $Cu_3Si$, that can destroy shallow junctions and contacts during thermal annealing steps and can result in degraded device performance or failure.

Effective barriers against Cu diffusion are critical because Cu interdiffusion results in an increase in contact and line resistance, a change in barrier height, formation of a leaky PN junction, embrittlement of the contact layer, and destruction of electrical connections to and throughout the chip. Metal nitride barriers can form reliable diffusion barriers and can provide low electrical resistivities relative to their pure metal counterparts. Titanium nitride (TiN) has been used as a diffusion barrier for aluminum, but displays poor performance for Cu metallization due to excessive interdiffusion. Tantalum nitride (TaN) has been a preferred diffusion barrier for Cu metallization. TaN requires a two-step chemical mechanical polishing (CMP) procedure that results in increased dishing of Cu surfaces and can scratch inter-layer dielectrics (ILDs). Dishing of the Cu is caused by a substantially higher CMP etch rate of Cu compared to TaN.

An alternative to TaN, tungsten nitride ($WN_x$) etches by a single CMP process and results in reduced Cu dishing because the CMP etch rates of Cu and $WN_x$ are more similar. It has been shown that $WN_x$ is an effective diffusion barrier against Cu penetration at temperatures up to about 750° C. As used herein, $WN_x$ is a line compound that includes tungsten nitride stoichiometric endpoints of $WN_2$ and $W_2N$. The predominant crystal structure of WN is hexagonal, $WN_2$ is rhombohedral, and $W_2N$ is a face centered cubic structure. $W_2N$ has the lowest resistivity of the three (50 μΩ-cm bulk resistivity). For example, a tungsten nitride film diffusion barrier between a tungsten plug and an adjoining Cu metallization layer on the surface of the wafer is shown in FIG. 1, where a tungsten plug 14 extends into a silicon substrate 10 with an overlying Cu layer 16 and an intervening diffusion barrier 12. Ever shrinking and increasingly more aggressive feature sizes in ICs require diffusion barriers that are highly conformal and mechanically and thermally stable. Deposition of conformal and continuous barrier layers of tungsten nitride with CVD at relatively low temperatures on high-aspect-ratio structures is not possible with current processes.

Two common methods for deposition of $WN_x$ include: physical deposition techniques, such as sputtering, and CVD, involving the reaction of tungsten halides with ammonia. Each of these methods has associated difficulties. Conventional physical vapor deposition technology involves reactive sputtering from a tungsten target in an atmosphere of gaseous nitrogen. Energized particle techniques, particularly sputtering, generally result in poor step coverage. Poor step coverage of the barrier layer can result in areas of excessively thin or missing barrier material in small features that have high aspect ratios. Sputter deposited layers are prone to the generation of high tensile stresses in adjacent layers that can cause interfacial defects.

Chemical vapor deposition processes for forming $WN_x$ can involve the reduction of tungsten halides by ammonia. This requires high deposition temperatures (>700° C.) which are incompatible with low dielectric materials and some metallization layers. The reaction byproducts, such as HF or HCl, are extremely corrosive and can rapidly etch other exposed device layers, including Si and $SiO_2$, and can decrease the operating lifetime of the processing equipment used for the deposition. Finally, adduct formation can result due to gas phase nucleation rather than chemical reaction at a wafer surface.

A single-source metal organic precursor molecule can be used for the MOCVD, or other suitable deposition technique, of tungsten nitride thin films. This can permit deposition at lower temperatures and allow a simplified reactor delivery system that avoids the possibility of adduct formation known to occur during the deposition of $WN_x$ from $WF_6$ and $NH_3$.

Chiu et al., *J. Mater. Res.* 1993, 8, 1353-1360 reports the use of a single-source metal-organic precursor, bis(tert-butylimido)bis(tert-butylamido)tungsten (t-BuN)$_2$W(NH-t-Bu)$_2$), to deposit a WN film. This precursor is a tungsten complex that has two imido ligands (=NR) covalently bonded to a tungsten. Deposition is carried out thermally over a temperature range of 450-650° C., with a very slow growth rate of 20-100 Å/min, to form a film of polycrystalline $W_2N$ with lattice parameters of 4.14-4.18 Å. The films have relatively high resistivities of 620-7000 μΩ-cm, with marginal step coverage of 50-85% for a 0.40 μm device feature.

McElwee-White et al., U.S. Pat. No. 6,596,888 reports a mono-imido tungsten precursor of the structure: $X_yL_{4-y}W$(NR), for example, $Cl_4(H_3CCN)W(N-i-Pr)$, as a single-source metal-organic precursor for the deposition of $WN_x$ films. MOCVD, at a temperature of 575-600° C. and at about 350 Torr, results in a $WN_x$ layer at a growth rate of approximately 940 Å/min with a layer having a bulk resistivity of 164 μΩ-cm. Auger analysis indicated that the film had the composition of 40-45% W, ~15% N, 5-10% O, and 30-35% C. Deposition at 700° C. and about 760 Torr yielded a $WN_x$ film that formed at a growth rate of approximately 3500 Å/min. The film displayed with a bulk resistivity of 1870 μΩ-cm. The film had a composition of 20-35% W, 10-15% N, 5-15% O and 45-52% C. Deposition at a temperature of 575° C. at approximately 350 Torr yielded a $WN_x$ film at a growth rate of approximately 900 Å/min, where the film displayed a bulk resistivity of 2016 μΩ-cm. The film had a composition of 49% W, 18% N, 15% C, and 17% O.

More recently other tungsten complexes with nitrogen-bound ligands have been examined as single source precursors, particularly: amides (Becker et al., *Appl. Phys. Lett.* 2003, 82, 2239-2241, Becker et al., *Chem. Mater.* 2003, 15, 2969-2976); imidos (Becker et al., *Chem. Mater.* 2003, 15, 2969-2976, Becker et al., *Chem. Mater.* 2003, 15, 2969-2976, Won et al., *J. Am. Chem. Soc.* 2006, 128, 13781-13788, Gwildies et al., *Inorg. Chem.* 2010, 49, 8487-8494, Bchir et al., *J. Am. Chem. Soc.* 2005, 127, 7825-7833, Bchir et al., *J. Cryst. Growth* 2003, 249, 262-274, Bchir et al., *J. Organomet. Chem.* 2003, 684, 338-350, El-Kadri et al., *Dalton Trans.* 2006, 1943-1953, Potts et al *Dalton Trans.* 2008, 5730-5736); amidinate (Gwildies et al., *Inorg. Chem.* 2010, 49, 8487-8494); guanidinate (Ajmera et al., *J. Vac. Sci. Technol., B* 2008, 26, 1800-1807, Rische et al., *Inorg. Chem.* 2006, 45, 269-277, Rische et al., *Surf. Coat. Technol.* 2007, 201, 9125-9130); and hydrazido (Koller et al., *Inorg. Chem.* 2008, 47, 4457-4462, McElwee-White et al., *Dalton Trans.* 2006, 5327-5333). Thermal decomposition of these complexes in the presence of the appropriate reductive co-reactant gas (usually $H_2$ or $NH_3$) typically resulted in $WN_xC_y$ films virtually free of oxygen and halogen. However, these precursors generally require high deposition temperatures (>350° C.) for the dissociation of C—N and/or N—N bonds that are present in these complexes. High temperatures can be problematic with many low-κ interfacial materials. The decomposition of hydrazido precursors to a $WN_xC_y$ film at temperatures can occur at about 300° C. Crystallization of amorphous $WN_xC_y$ films can occur at higher temperature, which can lead to reduced barrier layer performance due to the formation of grain boundaries.

Of the tungsten nitride barriers investigated, stoichiometries ranging from $W_2N$ to WN have been observed. Tungsten rich $WN_x$ barriers with a stoichiometry close to $W_2N$ have proven to be desirable due to a low resistivity and low Cu migration rate. Similarly, $WN_xC_y$ films that are tungsten rich, approaching $W_2NC$, have resulted in good Cu barriers with low resistivity. However, $WN_x$ or $WN_xC_y$ precursors that can be deposited at temperature less than 300° C. remain a goal for the preparation of diffusion barriers.

DETAILED DISCLOSURE

Figure 1:
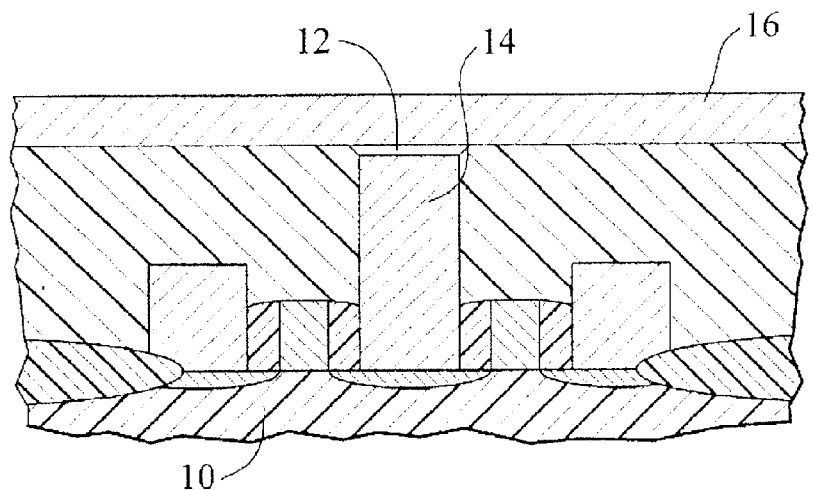
FIG. 1 shows a cross section through a prior art silicon device that illustrates the use of a barrier material to isolate plug material.

An embodiment of the invention is directed to the deposition of a $WN_x$ or $WN_xC_y$ precursor at temperatures less than 300° C. to form a $WN_x$ or $WN_xC_y$ barrier coating. In one embodiment of the invention, it was discovered that a $WN_x$ precursor, $WN(NMe_2)_3$ (1), can be deposited at temperatures below 300° C. According to an embodiment of the invention, the precursor complex contains a tungsten nitrido (W≡N) group to facilitate $WN_x$ or $WN_xC_y$ film formation by promoting a lower energy precursor decomposition process.

In an embodiment of the invention, the $WN_x$ or $WN_xC_y$ precursor is a tungsten nitrido complex of formula I:

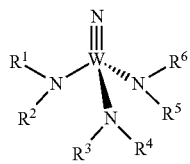

(I)

where $R^1$, $R^2$, $R^3$, $R^4$, $R^5$, and $R^6$ are independently H, $C_1$-$C_8$ alkyl, aryl, $C_1$-$C_8$ perfluoroalkyl, $C_1$-$C_8$ fluorohydroalkyl, or $SiR^{16}R^{17}R^{18}$, where $R^{16}$, $R^{17}$ and $R^{18}$ are independently H, $C_1$-$C_8$ alkyl, aryl, $C_1$-$C_8$ perfluoroalkyl, or $C_1$-$C_8$ fluorohydroalkyl.

In another embodiment of the invention, the $WN_xC_y$ precursor is a tungsten nitrido complex of formula II:

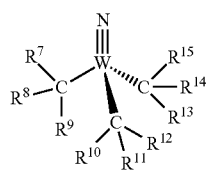

(II)

where $R^7$, $R^8$, $R^9$, $R^{10}$, $R^{11}$, $R^{12}$, $R^{13}$, $R^{14}$ and $R^{15}$ are independently H, $C_1$-$C_8$ alkyl, aryl, $C_1$-$C_8$ perfluoroalkyl, $C_1$-$C_8$ fluorohydroalkyl, or $SiR^{16}R^{17}R^{18}$, where $R^{16}$, $R^{17}$ and $R^{18}$ are independently H, $C_1$-$C_8$ alkyl, aryl, $C_1$-$C_8$ perfluoroalkyl, or $C_1$-$C_8$ fluorohydroalkyl.

In an embodiment of the invention, the $WN_x$ or $WN_xC_y$ precursor is a tungsten nitrido complex of formula III:

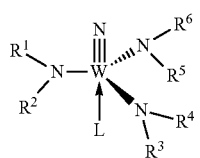

(III)

where $R^1$, $R^2$, $R^3$, $R^4$, $R^5$, and $R^6$ are independently H, $C_1$-$C_8$ alkyl, aryl, $C_1$-$C_8$ perfluoroalkyl, $C_1$-$C_8$ fluorohydroalkyl, or $SiR^{16}R^{17}R^{18}$, where $R^{16}$, $R^{17}$ and $R^{18}$ are independently H, $C_1$-$C_8$ alkyl, aryl, $C_1$-$C_8$ perfluoroalkyl, or $C_1$-$C_8$ fluorohydroalkyl, and where L is $C_1$-$C_8$ alkylnitrile, arylnitrile, heterocyclic aromatic amine, heterocyclic aliphatic amine and alkylamine ($NR^{19}R^{20}R^{21}$), where $R^{19}$, $R^{20}$, and $R^{21}$ are independently H, $C_1$-$C_8$ alkyl, aryl, $C_1$-$C_8$ perfluoroalkyl and $C_1$-$C_8$ partially fluorinated alkyl; or $SiR^{16}R^{17}R^{18}$, where $R^{16}$, $R^{17}$ and $R^{18}$ are independently H, $C_1$-$C_8$ alkyl, aryl, $C_1$-$C_8$ perfluoroalkyl, or $C_1$-$C_8$ fluorohydroalkyl.

In an embodiment of the invention, the $WN_x$ or $WN_xC_y$ precursor is a tungsten nitrido complex of formula IV:

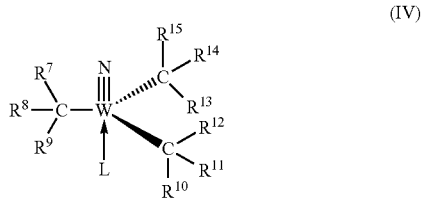

(IV)

where $R^7$, $R^8$, $R^9$, $R^{10}$, $R^{11}$, $R^{12}$, $R^{13}$, $R^{14}$ and $R^{15}$ are independently H, $C_1$-$C_8$ alkyl, aryl, $C_1$-$C_8$ perfluoroalkyl, $C_1$-$C_8$ fluorohydroalkyl, or $SiR^{16}R^{17}R^{18}$, where $R^{16}$, $R^{17}$ and $R^{18}$ are independently H, $C_1$-$C_8$ alkyl, aryl, $C_1$-$C_8$ perfluoroalkyl, or $C_1$-$C_8$ fluorohydroalkyl, and where L is $C_1$-$C_8$ alkylnitrile, arylnitrile, heterocyclic aromatic amine, heterocyclic aliphatic amine and alkylamine ($NR^{19}R^{20}R^{21}$) where $R^{19}$, $R^{20}$, and $R^{21}$ are independently H, $C_1$-$C_8$ alkyl, aryl, $C_1$-$C_8$ perfluoroalkyl, $C_1$-$C_8$ partially fluorinated alkyl; or $SiR^{16}R^{17}R^{18}$, where $R^{16}$, $R^{17}$ and $R^{18}$ are independently H, $C_1$-$C_8$ alkyl, aryl, $C_1$-$C_8$ perfluoroalkyl, or $C_1$-$C_8$ fluorohydroalkyl.

In an embodiment of the invention, the tungsten nitrido complex of formula I and/or III is used as a single source precursor for the deposition of $WN_x$ or $WN_xC_y$ at temperatures below 300° C. In another embodiment of the invention the tungsten nitrido complex of formula II and/or IV are used as a single source precursor for the deposition of $WN_xO_z$ or $WN_xC_yO_z$ at temperatures below 300° C. In an embodiment of the invention, the deposition of the $WN_x$ precursors of formula I, II, III, or IV results in a film. In another embodiment of the invention, the deposition from the $WN_x$ precursors of formula I, II, III, or IV results in nanoparticles.

Formation of the soluble and moderately volatile tungsten (VI) nitrido complex, 1, can be accomplished by reaction of $WN(O^tBu)_3$ (8) with $Zr(NMe_2)_4$ (9) in toluene through an amide/alkoxide exchange process. Prior art synthesis of 8 involves three steps, beginning from $WCl_4$ from the reduction of $WCl_6$. The synthesis involves reaction of $WCl_4$ with sodium amalgam and lithium dimethylamide to afford $W_2(NMe_2)_6$ (10). Alcoholysis of 10 leads to its tert-butoxide derivative $W_2(O^tBu)_6$ (11), which can be converted to a mixture of 8 and the alkylidyne complex, $WCMe(O^tBu)_3$ (12), by metathesis with acetonitrile. The yield of 8 is relatively low after purification by low temperature, high vacuum (~$10^{-4}$ Torr) sublimation to avoid decomposition.

Figure 2:
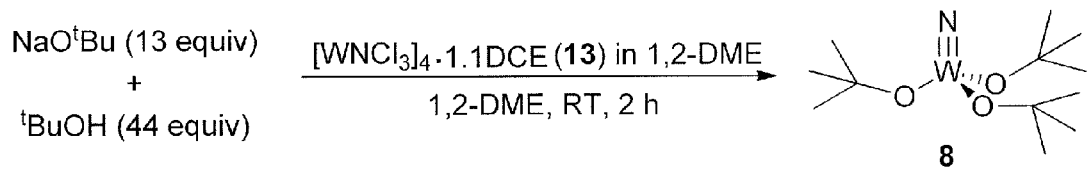
FIG. 2 shows a reaction scheme for the synthesis of the tungsten nitrido complex 1, according to an embodiment of the invention.
Figure 2:
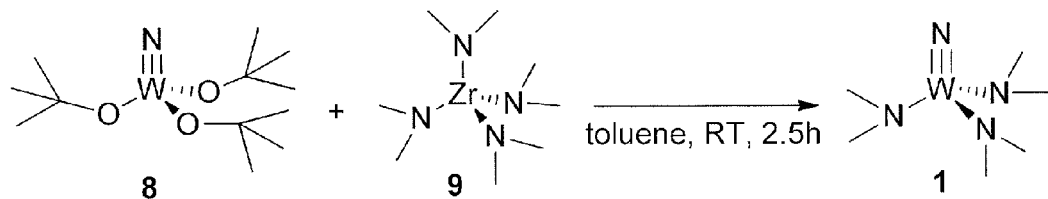

An efficient route to 8, according to an embodiment of the invention, uses $WCl_6$ as the W(VI) starting material. $WCl_6$ is converted to the tetramer $[WCl_3]_4 \cdot 1.1DCE$ (DCE=1,2-dichloroethane) (13) by treatment with trimethylsilyl azide, as disclosed in Close et al., *Inorg. Chem.* 1994, 33, 4198-4201. Reaction of 13 in excess tert-butanol and stoichiometric quantities of sodium tert-butoxide affords 8, in 52% yield, as shown in FIG. 2. Reaction of 8 with 9 in toluene gives crude 1 that could be purified by trituration with pentane, as shown in FIG. 2. Compound 1, obtained as a white solid, is highly sensitive to air and moisture. Darkening to a red-brown solid was observed under vacuum, and sublimation of 1 at 90-105° C. at $10^{-1}$ Torr is accompanied by decomposition. The $^1H$ and $^{13}C$ NMR spectra of 1 in benzene-d$_6$ indicate the chemical equivalence of all six methyl groups, consistent with (C$_{3v}$) symmetry and free rotation of the dimethylamide ligands.

Figure 3:
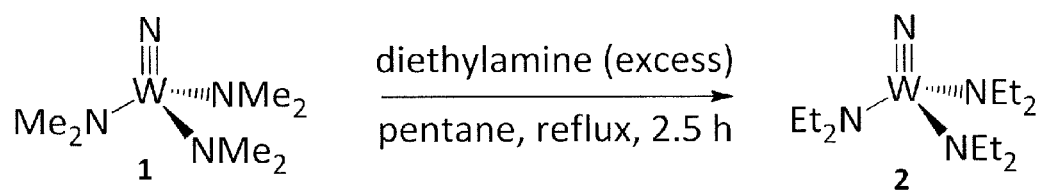
FIG. 3 shows a reaction scheme for the synthesis of the tungsten nitrido complex 2, according to an embodiment of the invention.

The separation of WN(NEt$_2$)$_3$, or other compounds of formula I with alkyl groups larger than methyl groups, from zirconium alkoxides formed during the synthesis, as illustrated in FIG. 2, is difficult when the zirconium alkoxide formed is Zr(O$^t$Bu)$_4$, or even Zr(OAdamantane)$_4$. According to an embodiment of the invention, the preparation of WN(NEt$_2$)$_3$, 2, and other WN(NR$_2$)$_3$ compounds is carried out by the transamination of 1, WN(NMe$_2$)$_3$, using various dialkylamines, that are less volatile that dimethylamine. For example, refluxing 1 with excess diethylamine results in nearly complete amine exchange to produce 2, as shown in FIG. 3. Compound 2 is readily purified by recrystallization from hexamethyldisiloxane.

Figure 4:
FIG. 4 shows a field emission scanning electron microscopy (FE-SEM) image of $WN_x$ nanoparticles obtained from 1 in benzene at a deposition temperature of 75° C., according to an embodiment of the invention.
Figure 5:
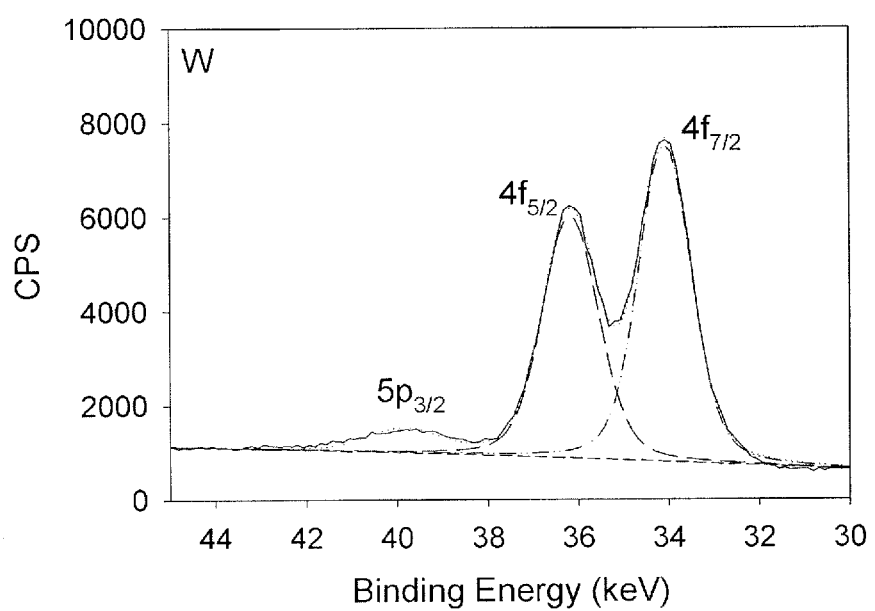
FIG. 5 shows XPS spectra of W 4f and $5p_{3/2}$ peaks for the $WN_x$ nanoparticles deposited from 1 at 75° C., according to an embodiment of the invention, with calculated fits to data shown as dotted lines.
Figure 6:
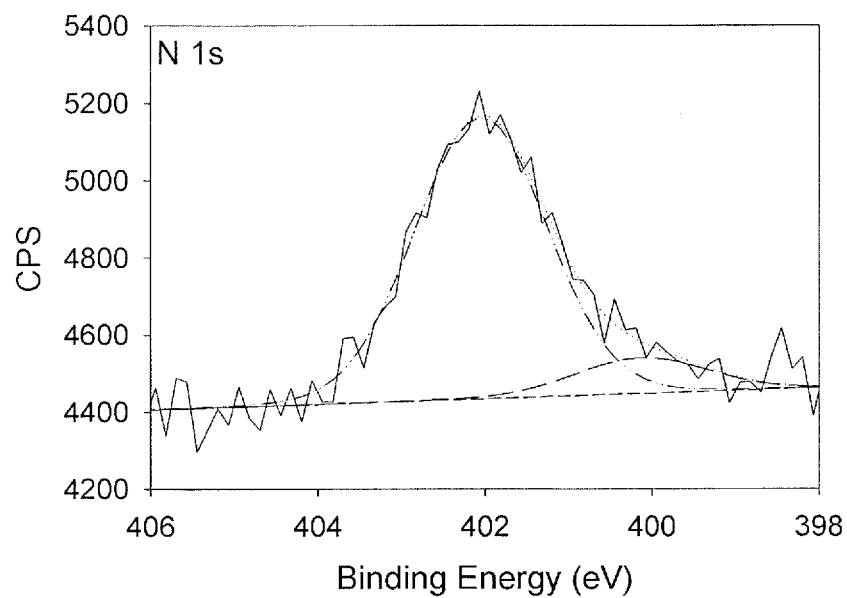
FIG. 6 shows X-ray photoelectron spectroscopy (XPS) spectra of N 1s peak for the $WN_x$ nanoparticles deposited using 1 at 75° C., according to an embodiment of the invention, with calculated fits to data shown as dotted lines.

In an embodiment of the invention, WN$_x$ or WN$_x$C$_y$ precursors I, II, III, and IV are single-source precursors for CVD to prepare WN$_x$ or WN$_x$C$_y$, as is described herein by the exemplary deposition of 1. Due to low volatility, deposition of 1 is performed in an aerosol-assisted CVD (AACVD) reactor, as disclosed below. Deposition of 1 can be carried out from 75 to 500° C. at 350 Torr. In an embodiment of the invention, nanospheres of WN$_x$ are deposited on a Si or other surface at low temperatures (75-125° C.) using an aerosol in benzene, with nanosphere diameters in the range 50 to 1300 nm and an average diameter of 500 nm. The variation in diameter and growth is consistent with a homogeneous nucleation process. Formation of prior art WN$_x$ nanoparticles has required high temperatures using thermolysis, pulsed laser-ablation, or 'urea glass' techniques. FIG. 4 shows a field emission SEM image of a WN$_x$ nanoparticle cluster obtained by delivering a 0.017 M solution of 1 in benzene at a substrate temperature of 75° C. FIG. 5 shows deconvoluted W 4f and 5p$_{3/2}$ peaks, and FIG. 6 shows the deconvoluted N 1s peak. The binding energies (BEs) of the W 4f$_{7/2}$ (34.0 eV), 4f$_{3/2}$ (36.1 eV) and 5p$_{3/2}$ (39.8 eV) indicate that partially oxidized WN$_x$ nanospheres are present on the substrate surface, most likely due to post-growth exposure to air. The N is spectrum confirms that WN$_x$ is partially oxidized; the deconvoluted spectra indicate that two species are present (BEs 400.2 and 401.6 eV). These BEs are higher than for unoxidized WN$_x$ (N1s 397 eV), and are assigned to oxidized WN$_x$. The O 1s spectrum also suggests that oxygen is bound to W (BE=530.3 eV) and to C (BE=532 eV) that is present in the deposited material.

Methods and Materials

General Procedures.

Unless otherwise specified, all manipulations were performed under an inert atmosphere (N$_2$, Ar) using standard Schlenk and glovebox techniques. Toluene and hexane were purified using an MBraun MB-SP solvent purification system and stored over 3 Å molecular sieves prior to use. Diethyl ether, tetrahydrofuran, benzene-d$_8$ and THF-d$_8$ were dried using sodium/benzophenone, distilled, and stored over 3 Å molecular sieves prior to use. Anhydrous 1,2-dimethoxyethane, tert-butanol and pentane were purchased from Sigma-Aldrich and stored over 3 Å molecular sieves in an inert atmosphere glovebox prior to use. Diethylamine, dipropylamine, diisopropylamine, N-ethylmethylamine and N-ethylisopropylamine were purchased and stored over activated 3 Å molecular sieves (15% w/v) for several days in an inert atmosphere glove box prior to use. [WNCl$_3$]$_4$·1.1 DCE was prepared using the method disclosed in Close et al., Inorg. Chem. 1994, 33, 4198-4201. All other chemicals were purchased and used as received. $^1$H and $^{13}$C NMR spectra were obtained using Gemini, Mercury, or VXR 300 MHz spectrometers using the residual protons of the deuterated solvents as reference peaks. Mass spectra were obtained with a Thermo Scientific Trace GC DSQ mass spectrometer using the DIP-CI mode of operation. As 1 did not undergo significant fragmentation, only the molecular ion is reported. Elemental analysis results were attained from Complete Analysis Laboratories.

Synthesis of WN(O$^t$Bu)$_3$ (8).

In the glovebox, 1.0 g (0.75 mmol) of bright orange [WNCl$_3$]$_4$·1.1 DCE and 50 mL of 1,2-dimethoxyethane were combined in a 100 mL Schlenk flask. After complete dissolution of the [WNCl$_3$]$_4$·1.1 DCE, this solution was transferred to an addition funnel. In a separate 100 mL Schlenk flask, tert-butanol (3.1 mL, 2.4 g, 33 mmol), sodium tert-butoxide (0.95 g, 9.9 mmol), and 5 mL of 1,2-dimethoxyethane were combined to form a white slurry. Using an addition funnel, the orange [WNCl$_3$]$_4$·1.1 DCE solution was added to the slurry dropwise over a period of 1 hour at room temperature. After complete addition, the slurry was stirred for an additional 1 h, and solvent was removed in vacuo. The crude solid was slurried in 50 mL of THF for 30 minutes, the solution filtered, and the remaining solid washed with THF (2×5 mL). Solvent was removed from the resulting light amber filtrate under vacuum at room temperature. The crude amber/white solid was slurried with 20 mL of diethyl ether for 15 min, and the slurry was filtered. The product was washed with diethyl ether (2×5 mL) to yield pure white WN(O$^t$Bu)$_3$ (0.65 g, 52%). Product identity was verified by comparison with literature data disclosed in Schrock et al., J. Am. Chem. Soc. 1982, 104, 4291-4293, Burroughs et al., Inorg. Chem. 2008, 47, 5377-5385 and/or Chisholm et al., Inorg. Chem. 1983, 22, 2903-2906.

Figure 7:
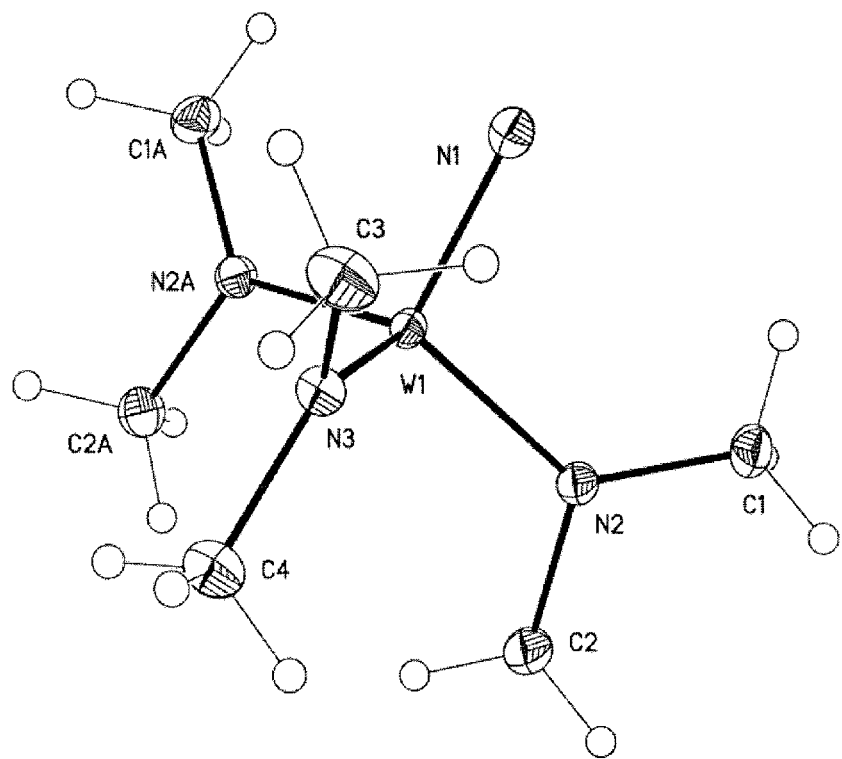
FIG. 7 shows a thermal ellipsoids diagram of the single crystal X-ray structure of 1, where thermal ellipsoids are drawn at 50% probability.

Synthesis of WN(NMe$_2$)$_3$ (1):

This procedure is a modification of a reported method in Greco, Ph.D. Dissertation, Massachusetts Institute of Technology (Cambridge, Mass.), 2001. In the glovebox, 0.17 g (0.63 mmol) of solid Zr(NMe$_2$)$_4$ and 25 mL of toluene were combined in a 50 mL Schlenk flask. After complete dissolution of the Zr(NMe$_2$)$_4$, 0.35 g (0.84 mmol) of pure white WN(O$^t$Bu)$_3$ was added to the clear reaction solution at room temperature. The resulting light yellow solution was stirred for 3 hours, and the solvent was removed under vacuum at room temperature. The crude amber residue was slurried in 15 mL of pentane for 15 min, and the slurry was filtered. The product was washed with pentane (2×7 mL) to yield pure white WN(NMe$_2$)$_3$ (0.23 g, 82.1%). $^1$H NMR (C$_6$D$_6$) δ 3.34 (s, 18H, —N(CH$_3$)$_2$). $^{13}$C NMR (C$_6$D$_6$) δ 51.19 (—N(CH$_3$)$_2$). DIP-CI-MS: Theoretical: [M+H]$^+$ 331.1120. Observed: [M+H]$^+$ 331.1084. Anal. Calcd for C$_6$H$_{18}$N$_4$W: C, 21.83; H, 5.50; N, 16.97. Found: C, 21.71; H, 5.58; N, 17.05. NMR spectra were similar to those reported in Greco. Crystals suitable for X-ray structure determination were obtained by vapor diffusion of pentane into a concentrated diethyl ether solution of 1 at low temperature. Compound 1 adopts a pseudo-tetrahedral geometry, as can be seen in the ORTEP representation in FIG. 7.

Crystallographic Structure Determination of 1.

X-ray intensity data were collected at 100 K on a Bruker DUO diffractometer using Mo—Kα radiation (λ=0.71073 Å) and an APEXII CCD area detector. Raw data frames were read by the program SAINT and integrated using 3D profiling algorithms. The resulting data were reduced to produce hkl reflections, their intensities, and estimated standard deviations. The data were corrected for Lorentz and polarization effects and numerical absorption corrections were applied based on indexed and measured faces. The structure was solved and refined in SHELXTL6.1, using full-matrix least-squares refinement. The non-H atoms were refined with anisotropic thermal parameters, and all of the H atoms were calculated in idealized positions and refined riding on their parent atoms. Molecules of the W complex are located on mirror planes. The protons of the methyl groups lying on those planes are disordered and each set was refined in two parts. In the final cycle of refinement, 1237 reflections (of which 1158 are observed with $I>2\sigma(I)$) were used to refine 64 parameters and the resulting $R_1$, $wR_2$ and S (goodness of fit) were 1.05%, 2.22% and 1.002, respectively. The refinement was carried out by minimizing the $wR_2$ function using $F^2$ rather than F values. $R_1$ is calculated to provide a reference to the conventional R-value but its function is not minimized.

Pertinent bond lengths and angles can be found in Table 1, below. The short W1-N1 distance for 1 (1.680(2) Å) compares favorably with other known terminal W(VI) nitride complexes. The W(VI) amide (W—N) bonds in 1 are somewhat shorter (W1-N2/W1-N2A 1.9512(17) Å, W1-N3 1.952(2) Å) than those found in [WN(N(Ar)$^i$Pr)$_3$] (Ar=3,5-C$_6$H$_3$Me$_2$) (W—N(Ar)$^i$Pr 1.972(3) Å), presumably from the lower steric bulk and stronger donor ($\sigma$, $\pi$) character of the dimethylamide ligands in 1. The sum of the bond angles around N2/N2A (359.97°) and N3 (359.96°) in compound 1 is essentially 360°, indicating sp$^2$ hybridization of the amide nitrogens. Deviation from tetrahedral geometry in 1 is manifested in the expansion of the N2-W1-N3/N2A-W1-N3/N2A-W1-N2 bond angles (114.58(6)°/114.58(6)°/113.89(10)°) and contraction of the N1-W1-N2A/N1-W1-N2/N1-W1-N3 bond angles (104.43(6)°/104.43(6)°/103.12(11)°) relative to 109.5°. Distortion towards trigonal pyrimidal geometry is consistent with steric repulsion between the amide methyl groups trans to N1, and the tendency for low overlap between bond forming orbitals.

TABLE 1

Selected bond lengths [Å] and angles [°] for 1.

| W1-N1 | 1.680(2) | N2A-W1-N2 | 113.89(10) |
|---|---|---|---|
| W1-N2A | 1.9512(17) | N1-W1-N3 | 103.12(11) |
| W1-N2 | 1.9512(17) | N2A-W1-N3 | 114.58(6) |
| W1-N3 | 1.952(2) | N2-W1-N3 | 114.58(6) |
| N2-C1 | 1.457(2) | C1-N2-C2 | 111.52(16) |
| N2-C2 | 1.469(3) | C1-N2-W1 | 129.01(13) |
| N3-C4 | 1.465(3) | C2-N2-W1 | 119.44(13) |
| N3-C3 | 1.466(4) | C4-N3-C3 | 110.9(2) |
| N1-W1-N2A | 104.43(6) | C4-N3-W1 | 120.68(19) |
| N1-W1-N2 | 104.43(6) | C3-N3-W1 | 128.38(18) |

Synthesis of WN(NEt$_2$)$_3$ (2):

In a 100 mL Schlenk flask, 2.22 g of 1 and 40 mL of pentane were combined to create a white slurry. To the slurry, 21 mL of diethylamine was added all at once to give an orange/red suspension within minutes. A reflux condenser was attached and the reaction mixture was brought to a gentle reflux under argon. After 3 h, the resulting light amber solution was returned to room temperature and all volatiles were removed under vacuum. The remaining rusty/tan residue was extracted by stirring with hexamethyldisiloxane (10 mL) for 15 minutes, filtered through Celite™, and the filter pad was washed with additional hexamethyldisiloxane (2×5 mL). The resulting amber filtrate was concentrated to saturation under vacuum and placed in the glove box refrigerator overnight to yield white needles. The mother liquor was removed by pipet, and the pure product was dried under vacuum to yield 2.37 g of analytically pure 2 (85%). $^1$H NMR (C$_6$D$_6$, 300 MHz): δ=1.16 [t, 18H, —N(CH$_2$CH$_3$)$_2$]; 3.58 [q, 12H, —N(CH$_2$CH$_3$)$_2$]. $^{13}$C NMR (C$_6$D$_6$, 300 MHz): δ=17.83 [—N(CH$_2$CH$_3$)$_2$]; 52.57 [—N(CH$_2$CH$_3$)$_2$]. DIP-CI-MS: calcd. for [M+H]$^+$ 415.2060. found 415.2062.

Synthesis of WN(N(Me)Et)$_3$ (3):

In a 10 mL Schlenk flask, 0.25 g of 1 and 3.0 mL of N-ethylmethylamine were combined to create an orange/red suspension within minutes. A reflux condenser was attached and the reaction mixture was brought to a gentle reflux under argon. After 2.5 h, the resulting orange/amber solution was cooled to room temperature and volatiles were removed under vacuum. The rusty/tan residue was extracted by stirring with pentane (~7 mL) for 15 minutes, filtered through Celite™, and the filter pad was washed with additional pentane (2×3 mL). Volatiles were removed from the amber filtrate under vacuum. The crude product was dissolved in hexamethyldisiloxane, concentrated to saturation, and placed in the cold-box overnight to yield a white precipitate. The mother liquor was removed by pipet, and the pure product was dried under vacuum to yield 0.15 g of analytically pure WN(N(Me)Et)$_3$ (54%).

Synthesis of WN(N(Et)$^i$Pr)$_3$ (4):

In a 25 mL Schlenk flask, 0.26 g of 1 and 12 mL of hexane were combined to create a white slurry. To the slurry, 3.0 mL of N-ethylisopropylamine was added rapidly to give an orange/red suspension (some white precipitate) within several minutes. A reflux condenser was attached and the reaction mixture was brought to a gentle reflux under argon. After 3.5 h, the resulting dark brown/amber solution was cooled to room temperature and volatiles were removed under vacuum to leave a tan/brown solid residue. The residue was extracted by stirring with hexamethyldisiloxane (5 mL) for 15 minutes, filtered through Celite™, and the filter pad was washed with additional hexamethyldisiloxane (2×3 mL). The resulting dark amber filtrate was concentrated to saturation under vacuum and cooled overnight to yield a white/tan precipitate. The mother liquor was removed by pipet, and the product was dried under vacuum to yield mostly pure (>90% by $^1$H NMR) WN(N(Me)Et)$_3$. The product was recrystallized again with minimal hexamethyldisiloxane to yield analytically pure WN(N(Me)Et)$_3$.

Synthesis of WN(N($^n$Pr)$_2$)$_3$ (5):

In a 25 mL Schlenk flask, 0.25 g of 1 and 12 mL of pentane were combined to create a white slurry. To the slurry, 3.0 mL of dipropylamine was added rapidly to give an orange/red suspension within minutes. A reflux condenser was attached and the reaction mixture was brought to a gentle reflux under argon. After 18 h, the resulting orange/red solution was cooled to room temperature and volatiles were removed under vacuum to leave a tan solid residue. The residue was extracted by stirring with hexamethyldisiloxane (7 mL) for 15 minutes, filtered through Celite™, and the filter pad was washed with additional hexamethyldisiloxane (2×3 mL). The resulting amber filtrate was concentrated to saturation under vacuum and placed in the cold-box overnight to yield white needles. The mother liquor was removed by pipet, and the pure product was dried under vacuum to yield analytically pure WN(N($^n$Pr)$_2$)$_3$.

Synthesis of WN(NMe$_2$)$_2$(N$^i$Pr$_2$) (6):

In a 100 mL Schlenk flask, 250 mg (0.647 mmol) of 1 was dissolved in 60 mL pentane. To the solution about 3 mL of diisopropylamine was added. A reflux condenser was attached and the entire setup was connected to a Schlenk line under argon atmosphere. The solution was refluxed in pentane for 12 h under argon, and then the solvent was removed under vacuum at room temperature. The product was extracted with hexamethyldisiloxane and filtered through Celite™ to give a brown filtrate which was concentrated and left for crystallization in the glove box refrigerator for overnight to give colorless crystals of 6. (65%). $^1$H NMR ($C_6D_6$, 300 MHz): δ=1.31 [d, J=6.43 Hz, 12H, N(CH($CH_3$)$_2$)$_2$]; 3.35 [s, 12H, N($CH_3$)$_2$]; 3.41 [m, J=6.43 Hz, 2H, N(CHMe$_2$)$_2$]. $^{13}$C NMR ($C_6D_6$, 300 MHz): δ=26.39 [N(CH($CH_3$)$_2$)$_2$]; 51.34 [N($CH_3$)$_2$]; 51.89 [N(CHMe$_2$)]. DIP-CI-MS: calcd. for [M+H]$^+$ 387.1747. found 387.1750.

Synthesis of WN(NMe$_2$)(N$^i$Pr$_2$)$_2$ (7):

In a 100 mL Schlenk apparatus, 500 mg (1.131 mmol) of 1 was dissolved in ~10 mL of diisopropylamine. A reflux condenser was attached and the entire setup was connected to a Schlenk line under argon atmosphere. The solution was refluxed for 12 h under argon, and then the solvent was removed under vacuum at room temperature. The product was extracted with hexamethyldisiloxane and filtered through Celite™ to give a brown filtrate which was concentrated and left for crystallization in the glove box refrigerator for overnight to give colorless crystals of 7 (65%). $^1$H NMR ($C_6D_6$, 300 MHz): δ=1.32 [dd, J=6.39, 23.56 Hz, 24H, N(CH($CH_3$)$_2$)$_2$]; 3.37 [s, 6H, N($CH_3$)$_2$]; 3.45 [m, J=6.39 Hz, 4H, N(CHMe$_2$)$_2$]. $^{13}$C NMR ($C_6D_6$, 300 MHz): δ=27.17 [N(CH($CH_3$)$_2$)$_2$]; 51.37 [N($CH_3$)$_2$]; 52.27 [N(CHMe$_2$)]. DIP-CI-MS: calcd. for [M+H]$^+$ 443.2368. found 443.2364.

Synthesis of WN(NEt$_2$)$_2$(N$^i$Pr$_2$) (15):

In a 100 mL Schlenk apparatus, 250 mg (0.565 mmol) of 6 was dissolved in about 60 mL pentane. To the solution, 3 mL of diethylamine was added. A reflux condenser was attached and the entire setup was connected to a Schlenk line under argon atmosphere. The solution was refluxed for 12 h under argon, and then the solvent was removed under vacuum at room temperature. The product was extracted with hexamethyldisiloxane and filtered through Celite to give a brown filtrate which was concentrated and left for crystallization in the glove box refrigerator for overnight to give colorless crystals of 15 (60%). $^1$H NMR ($C_6D_6$, 300 MHz): δ=1.15 [t, J=7.01 Hz, 12H, N($CH_2CH_3$)$_2$]; 1.34 [d, J=6.43 Hz, 12H, N(CH($CH_3$)$_2$)$_2$]; 3.42 [m, J=6.43 Hz, 2H, N(CHMe$_2$)$_2$]; 3.51-3.72 [m, J=7.01 Hz, 8H, N($CH_2CH_3$)$_2$]. $^{13}$C NMR ($C_6D_6$, 300 MHz): δ=17.59 [N($CH_2CH_3$)]; 26.62 [N(CH($CH_3$)$_2$)$_2$]; 51.24 [N($CH_2CH_3$)$_2$]; 52.71 [N(CHMe$_2$)]. DIP-CI-MS: calcd. for [M+H]$^+$ 443.2373. found 443.2366.

WN(NEt$_2$)(N$^i$Pr$_2$)$_2$ (16).

In a 100 mL Schlenk apparatus, 250 mg (0.532 mmol) of 7 was dissolved in about 60 mL benzene. To the solution, 3 mL of diethylamine was added. A reflux condenser was attached and the entire setup was connected to a Schlenk line under argon atmosphere. The solution was refluxed for 12 h under argon, and then the solvent was removed under vacuum at room temperature. Sublimation was carried out with the crude at 60° C. under 240 mTorr vacuum pressure to give orange colored 16 in pure form. (50%). $^1$H NMR ($C_6D_6$, 300 MHz): δ=1.15 [t, J=6.87 Hz, 6H, N($CH_2CH_3$)$_2$]; 1.33 [dd, J=6.00, 21.00 Hz, 24H, N(CH($CH_3$)$_2$)$_2$]; 3.46 [m, J=6.00 Hz, 4H, N(CHMe$_2$)$_2$]; 3.62 [q, J=6.87 Hz, 4H, N($CH_2CH_3$)$_2$]. $^{13}$C NMR ($C_6D_6$, 300 MHz): δ=17.21 [N($CH_2CH_3$)]; 26.79 [N(CH($CH_3$)$_2$)$_2$]; 51.43 [N($CH_2CH_3$)$_2$]; 52.66 [N(CHMe$_2$)]. DIP-CI-MS: calcd. for [M+H]$^+$ 471.2687. found 471.2705.

CVD Experimental Apparatus.

A custom-built, vertical cold-wall impinging-jet aerosol-assisted chemical vapor deposition (AACVD) reactor was used to explore deposition of WN$_x$ using 1. Si(100) and Si(111) substrates (acquired from Cemat Silicon and Crysteco, respectively) were prepared by sequential dipping in boiling trichloroethylene, boiling acetone, and boiling methanol for 3 minutes each, followed by a 30 sec rinse in boiling deionized water, and a 2 minutes buffered oxide etch. Small area substrates of each orientation were then loaded onto the graphite susceptor and the reactor pressure was reduced to a base pressure of at least 400 mTorr for ~10 minutes. The system was then purged with 1 slm N$_2$ (99.999% purity) flow for 30 minutes at an operating pressure of 350 Torr. Subsequently, the substrate temperature was raised to approximately 1000° C. under pure H$_2$ ambient for 15 minutes to reduce oxides and remove residual organic surface contamination. The substrate temperature was reduced to the desired operating value. A gastight Hamilton syringe (part number 81656) was used to transfer 10 mL of a 0.017 M solution of 1 in benzene. A Cole-Parmer syringe pump delivered the precursor solution through $^1/_{16}$" Tygon tubing to a Cetac nebulizer unit at a rate of 4 mL/hr. The nebulizer system contained a heated quartz plate that vibrates at a rate of 1.44 MHz, which facilitated the production of a solvent/precursor aerosol. The aerosol mixture was transported to the reaction chamber via 1 slm flow of N$_2$ gas through stainless steel tubing maintained at 50° C. After complete delivery of the precursor solution, the samples were removed and characterized for composition and morphology by XRD, XPS, AFM, SEM, and EDS. These instruments are maintained by the Major Analytical Instrumentation Center at the University of Florida. The XPS data were obtained on a Perkin-Elmer 5600 ESCA system using an Al—Kα (E$_p$=1486.7 eV) source.

Substrate Preparation:

The substrates used for WC$_x$N$_y$ deposition were p-type boron-doped Si(100) and n-type arsenic-doped Si(111) wafers. The Si(100) substrates were acquired from Cemat Silicon and the Si(111) substrates from Crysteco. The wafers were cut to 1 cm×1 cm, and bathed in a series of degreasing chemicals and an oxide etchant. The substrates were treated for 3 minutes each in boiling trichlorocthylene, boiling acetone, and boiling methanol to remove any organic contamination on the surface and subsequently rinsed for 30 seconds in boiling deionized water for residual solvent removal. Afterward, the substrates were placed in a buffered-oxide-etchant (6:1 NH$_4$F:HF in water) for 2 minutes to remove the native surface oxide and leave a relatively air-stable hydrogen terminated surface. The samples were blown dry using 99.999% nitrogen, wiped with an acetone soaked lint-free alpha swab, and blown dry again.

WC$_x$N$_y$ from 1

WC$_x$N$_y$ Film Growth from 1:

Owing to the low volatility of 1, an in-house built aerosol-assisted chemical vapor deposition reactor was used for the deposition studies. The three gases employed: N$_2$ (99.999% from Airgas South); hydrogen (99.999% from Airgas South); and anhydrous ammonia (from Alphagaz); were controlled using MKS mass flow controllers and delivered through ¼ inch stainless steel (SS) piping. Gasses were directed to a Cetac Technologies nebulizer unit equipped with a heated and vibrating (≈100° C. at 1.44 MHz) piezoelectric quartz plate, to aerosolize and transport the 0.051 M solution of the precursor 1 in pyridine. The liquid precursor solution of 1 was delivered from a gas-tight Hamilton syringe to the nebulizer by a Cole-Parmer syringe pump where the solution passed through a 25 psi poppet valve to prevent vaporization upon vacuum exposure. The precursor solution mist was carried through lines to the reaction zone dispersed by a vertically impinging showerhead positioned 6 cm above the heated substrates.

The reactor body consists of an arrangement of 316 SS Conflat flanges configured into 5-way tee (all at 900 angles)

that rests upon a beveled collar, which compresses a Viton o-ring into the fused quartz cylinder (63 mm ID) that defines the reactor volume. The same sealing mechanism exists at the bottom of the reaction chamber and both o-rings are cooled by a water jacket. The reaction chamber houses the silicon substrates that rest atop a centerline-bored graphite susceptor hoisted by a type-K thermocouple encased by an alumina ceramic tube. A thermocouple tip was positioned approximately 2 mm beneath the substrate surface for accurate temperature measurement. The susceptor was inductively heated by Cu RF coils extending from a Westinghouse RF generator. The substrates were conductively heated.

The reactor effluent traveled through a port located on the bottom bracket of the reactor volume and passed through a Pyrex™ particulate catch before making way to a pressure controlling MKS throttling valve before exiting through the Fisher-Scientific Maxima C pump connected to a scrubbed exhaust. System pressures above 1 Torr were measured by an MKS Baratron pressure gauge and pressures below 1 Torr were evaluated using a Sensavac Pirani gauge.

Cleaned substrates were placed onto the graphite susceptor and loaded into the reactor through a front-mounted door. The alumina casing of the thermocouple was inserted into the centerline bore of the susceptor where the substrates were positioned to the RF coils' height for heating. The reactor was sealed and evacuated to a minimum pressure of at least 400 mTorr. The $N_2$ carrier gas was turned on and the reactor volume was purged with 1000 standard-cubic-centimeters per minute (sccm) and subsequently brought to its operating pressure via the throttling valve downstream of the reaction chamber. The RF generator was turned on and its power increased step-wise to bring the substrate temperature to at least 1000° C., under $N_2$ flow. $H_2$ was turned on at 1000 sccm as the $N_2$ was shut off for 15 minutes to provide a reducing atmosphere for the oxides and residual organic substances on the surface of the substrates. After 15 minutes, the nitrogen carrier gas was selected and the temperature is lowered to the operating temperature. The precursor syringe pump was started at a rate of 4 mLhr$^{-1}$ and the nebulizer was turned on for the duration of the experiment, typically 150 minutes, but the length varied with desired film thickness and concentration of the precursor in the solvent.

Diffusion Barrier Testing:

Complex 1 was used to deposit films for Cu diffusion barrier applications. A film of 300 nm of MOCVD Cu was deposited onto freshly prepared $WC_xN_y$/Si with approximately 5 minutes of post-growth exposure to air. The Cu films were deposited using (hfac)Cu$^{I,II}$(TMVS) as the Cu source in an in-house MOCVD reactor, and subsequently annealed at a temperature of at least 500° C. for a minimum of 30 minutes under 99.999% $N_2$ flow (to prevent Cu oxidation and to limit film outgassing). The annealed Cu/$WC_xN_y$/Si stacks were then investigated by XRD, SEM, and 4PP to verify their intactness. XRD measurements can indicate barrier failure by the onset of $Cu_3Si$ peaks. Cross-sectional SEM was used for visual inspection of the interfaces in conjunction with EDS compositional mapping and etch-pit analysis. Etch-pit testing is performed by removing the Cu layer with a dilute nitric acid solution, then removing the barrier with a solution of $NH_4OH$, $H_2O_2$, and $H_2O$ in a ratio of 1:1:4 for 10 minutes, followed by the etching of $Cu_3Si$ for 5 seconds with Secco etchant [($K_2Cr_2O_7$:$H_2O$, 1:1):HF,1:1]. If the barrier fails, using the etch-pit test will yield inverse pyramidal pits on the surface of the substrate.

Figure 8:
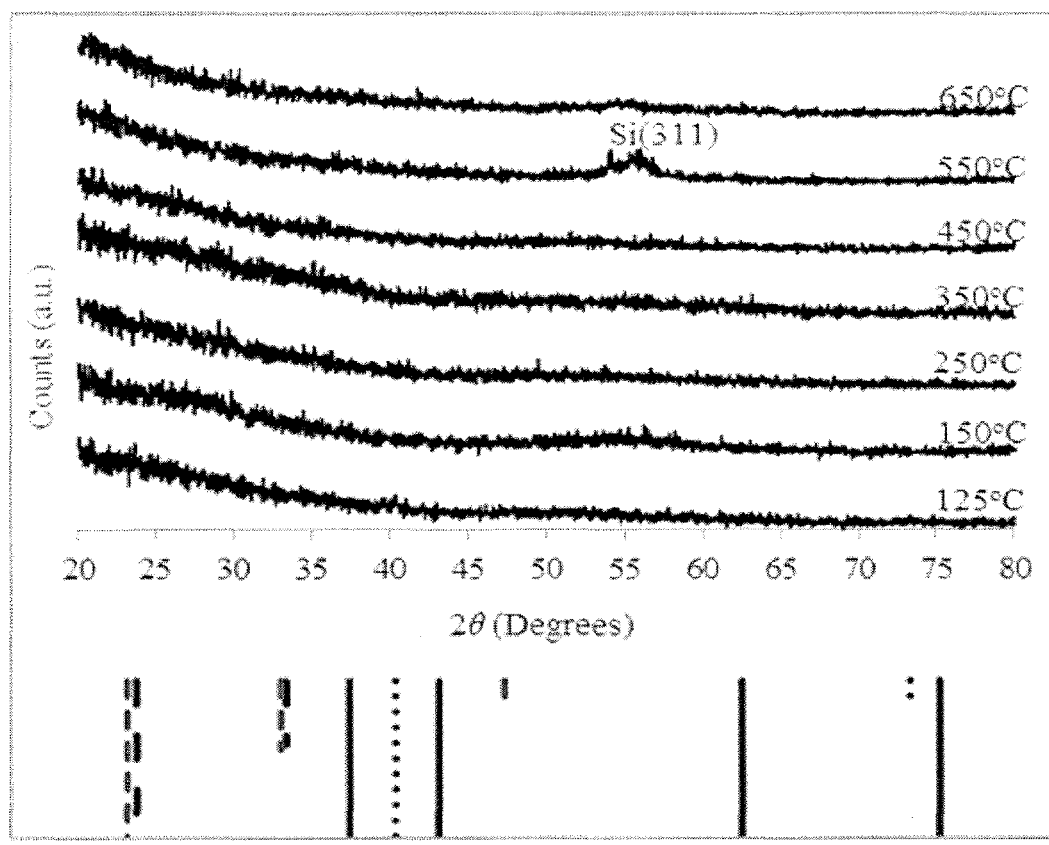
FIG. 8 shows GIXD data taken for $WN_xC_y$ films deposited using compound 1 at temperatures from 125 to 650° C., according to an embodiment of the invention.

$WC_xN_y$ Film Microstructure:

$WC_xN_y$ films grown using a solution of 1 in pyridine (0.051 M) at a nominal operating pressure of 350 Torr resulted in film thicknesses of less than 150 nm. To ensure a high signal-to-noise ratio, grazing incidence x-ray diffraction (GIXD) was employed over the traditional powder XRD. A Philips X'Pert MRD system was used to perform the diffraction scans. FIG. 8 displays GIXD spectra from depositions at temperatures ranging from 125 to 650° C. The depositions using 1 as a single-source precursor yield highly amorphous thin films with no preferred crystal texturing. The lone peak at a deposition temperature of 550° C. appears to be an anomaly and is the Si (311) peak. The line pattern under the spectra represents typical values for various crystal planes associated with $WC_xN_y$, where the solid lines, from left to right, represent signals associated with (111), (200), (220), and (311) planes of β-$WC_xN_y$.

Figure 9:
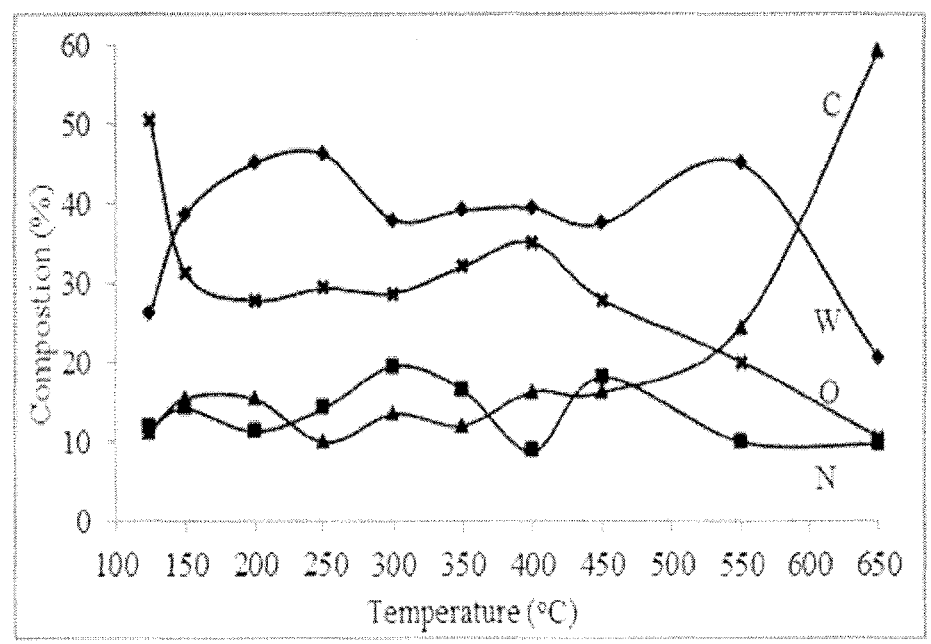
FIG. 9 shows a plot of the $WN_xC_y$ film composition from deposition of compound 1 at various temperatures, according to an embodiment of the invention.

$WC_xN_y$ Film Compositions:

Valence states of each component of the β-$WC_xN_y$ films were evaluated with X-ray photoelectron spectroscopy (XPS) using a Perkin-Elmer PHI 5100 ESCA System with an Al anode (hv=1486.3 eV). The XPS system had a nominal sputter rate of 4 Å/min. The deconvolution of XPS spectra was performed using RBD Analysis Suite software. FIG. 9 shows plots of the relative atomic concentrations existing in the films for various deposition temperatures.

Figure 10:
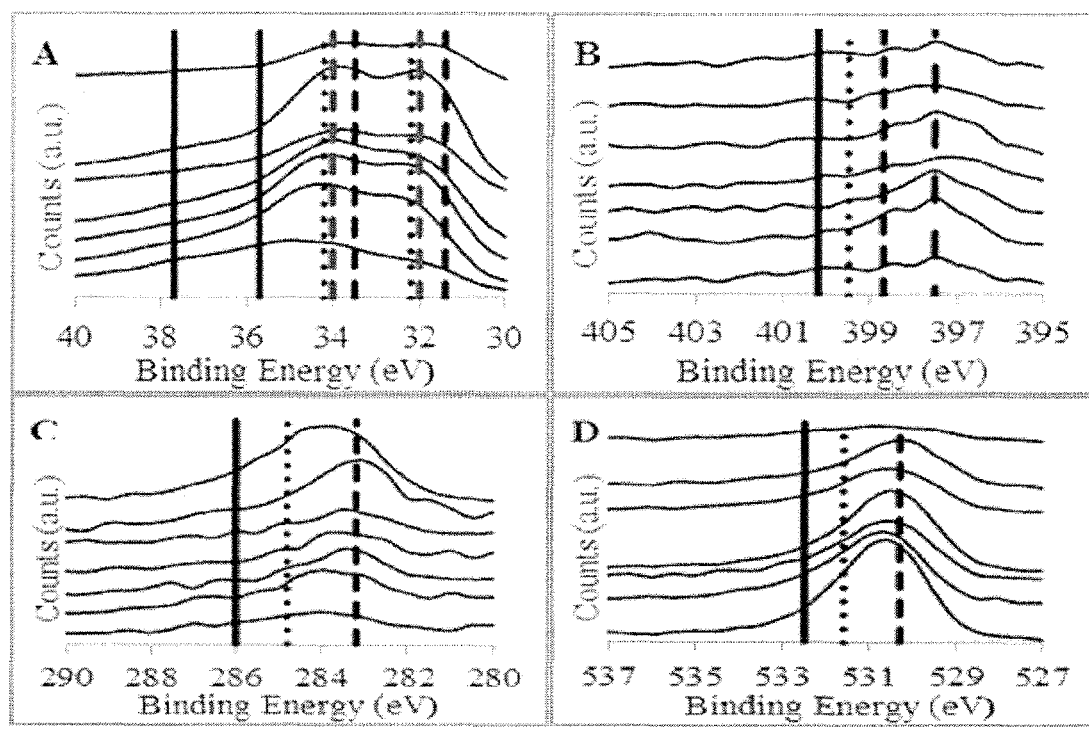
FIG. 10 shows plots of binding energies for a) W4f, b) N 1s; c) C 1s, and d) O 1s in $WN_xC_y$ films deposited using compound 1, over the range of temperatures indicated in FIG. 8, according to an embodiment of the invention.

FIG. 10 shows plots of the evolution of the primary elemental XPS peaks with increasing deposition temperature. The superimposed line patterns identify typical binding energies for relevant valence states associated with each respective element. In FIG. 10a, coupled values are observed for W doublet peaks, W $4f_{7/2}$ and W$4f_{5/2}$. The plots of films at various temperatures have the same profile and temperatures as that of FIG. 8, where the lowest deposition temperature (125° C.) is represented by the curve on the bottom of the plots, and the highest deposition temperature (650° C.) is at the top of the plot. With increasing deposition temperature, the W 4f peak shifts from higher binding energies (BE) to lower energies, suggesting a transition from a higher oxidation state to a lower one. Typical BE's for the most thermodynamically stable tungsten oxide, $WO_3$, reside around 35.7 eV and 37.7 eV for the W $4f_{7/2}$ and W$4f_{5/2}$ peaks, respectively. FIG. 10a displays these values with the solid vertical lines. The finely hashed lines represent the $WN_x$ binding energies at 32.2 eV and 34.2 eV, where the adjacent hashed line represents the $WC_{1-x}$ binding energies at 32.0 eV and 34.0 eV, and the more distant hashed line represent W metal binding energies at 31.4 eV and 33.5 eV, all respective to the W $4f_{7/2}$ and W$4f_{5/2}$ peaks. The progression of peaks through higher deposition temperatures, suggests deposition as predominantly $WC_xN_y$ solid solution.

The N 1s peak position is consistently at a BE of 397.5 eV for all deposition temperatures, implying it is W bound. The solid line in FIG. 10b at 400.2 eV indicates a C—N bond, the finely hashed line at 399.5 eV represents "free" N (generally at grain boundaries), the hashed line at 398.7 eV suggests a $WO_xN_y$ solid solution, and the broadly hashed line suggests $WN_x$.

FIG. 10c contains a solid line at 286 eV for a C—N bond, a finely hashed line at 284.8 eV for "free" C (i.e. adventitious), and a hashed line at 283.2 eV for $WC_{1-x}$. At lower temperatures (<250° C.) the carbon was observed purely in a carbide state. At intermediate temperatures (250° C.<T<500° C.) the carbon predominatey resided in a carbide (~90%) form and to a lesser extent as adventitious carbon (~10%). Above 500° C. the adventitious carbon content increased linearly until 650° C. where it was maximized at 45%.

FIG. 10d illustrates the different BE's for relevant oxide compounds. Oxygen exists in the film as an impurity resulting from post-growth exposure to air as well as the uncharacteristically low growth rates for CVD. The films were of relatively low density which permitted a high in-diffusion of oxygen upon exposure to atmosphere. Additionally, apparently due to imperfect vacuum seals, a partial pressure of oxygen in the reactor lends to a higher incorporation of oxide impurity at lower growth rates. The solid line at 532.5 eV is related to $SiO_2$, the finely hashed line at 531.6 eV indicates "free" $O_2$, and the hashed line at 530.3 eV indicates $WO_3$. At lower temperatures (<250° C.) the O signal is primarily results from the in-diffusion of gaseous $O_2$ upon air exposure, whereas at temperatures above 250° C. $WO_3$ is predominant as it forms during film deposition. Overall, some oxygen incorporation is believed to improve the effectiveness of barrier layer.

Figure 11:
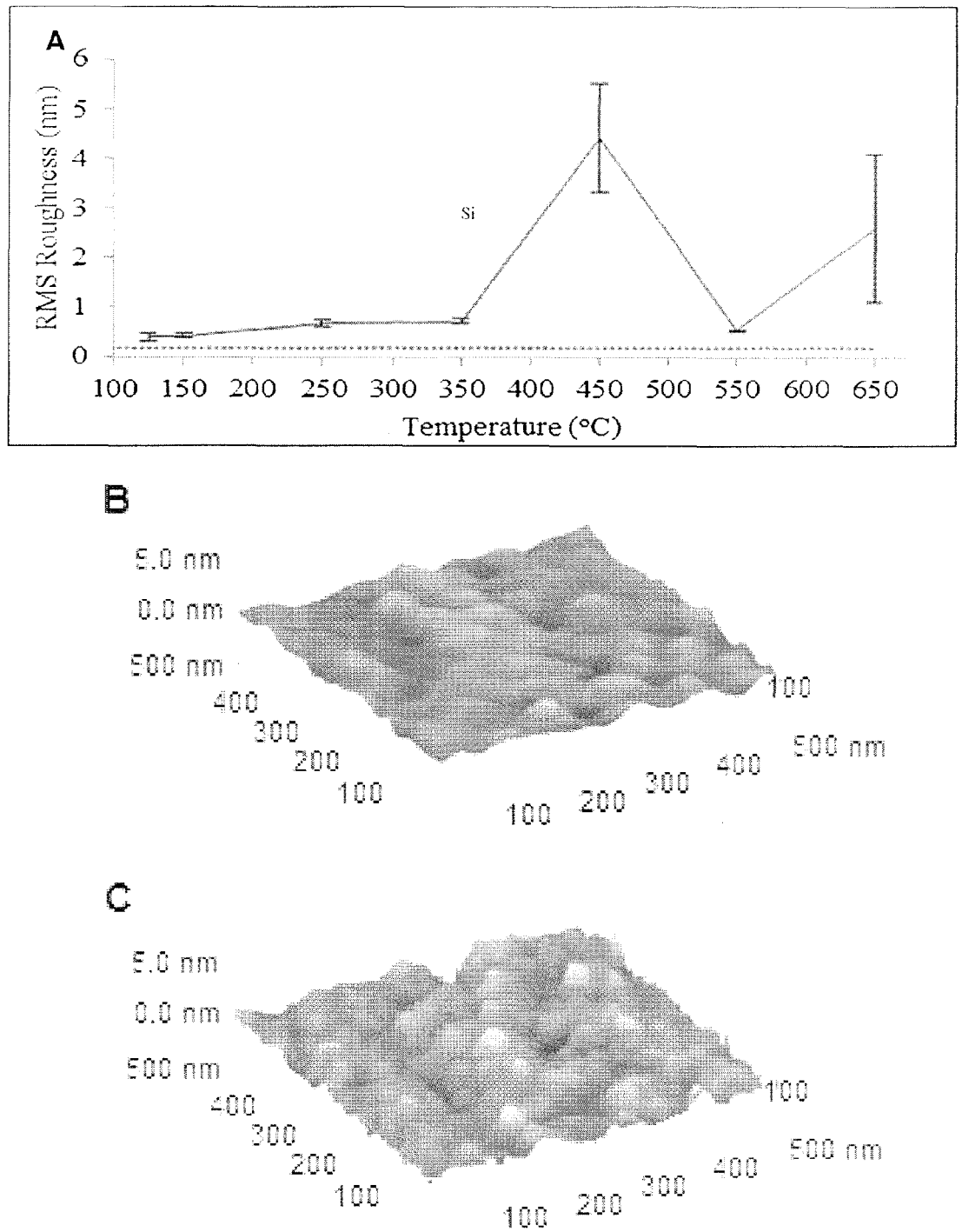
FIG. 11 shows: a) a plot of surface roughness for $WN_xC_y$ films formed at different deposition temperatures; b) an AFM micrograph for a $WN_xC_y$ film deposited at 150° C., according to an embodiment of the invention; and c) an AFM micrograph for a $WN_xC_y$ film deposited at 550° C.

$WC_xN_y$ Film Surface Roughness:

A VEECO Dimension 3100 Atomic Force Microscope (AFM) was used to perform root-mean-square (RMS) surface roughness measurements. Films deposited using 1 resulted in highly smooth films with RMS roughness values nearing that of the underlying Si substrate (1.8 Å), as shown in FIG. 11a. FIG. 11b shows the morphology of the films deposited at 150° C., whereas FIG. 11c shows the morphology of films deposited at 550° C. The smooth surface promotes strong adhesion for Cu deposition and limits the amount of interfacial resistance via electron scattering.

Figure 12:
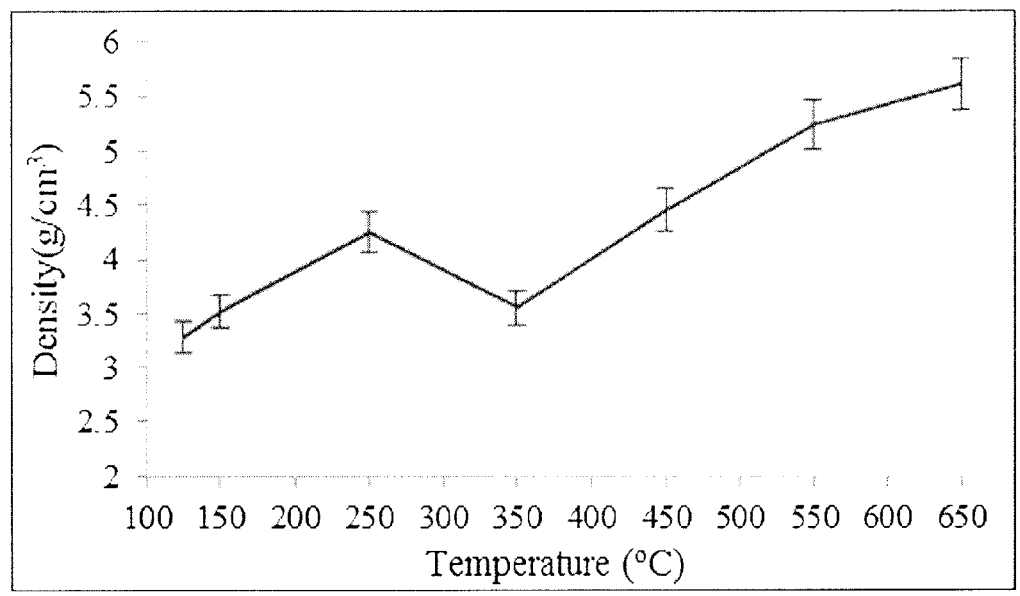
FIG. 12 shows a plot of $WN_xC_y$ film densities for depositions from 1 carried out at a variety of temperatures, according to an embodiment of the invention.

$WC_xN_y$ Film Density Measurements:

Films deposited using 1 were analyzed with XRR measurements to determine film densities as a function of deposition temperature. XRR measurements were performed using a Philips X'Pert MRD system with density information derived from the critical angle, $\theta_c$, in the 2θ scans. FIG. 12 shows the density dependence with temperature, clearly displaying a densification of films with increasing deposition temperature, as is typical of CVD type growth as surface diffusion increases which facilitates alignment of crystallites to their lowest energy states. Typical bulk values for crystalline $WC_xN_y$ have been reported between 15.63-18.6 $g/cm^3$ whereas bulk values for amorphous $WC_xN_y$ have been reported between 6.8-12.0 $g/cm^3$ for CVD growth mechanisms. Despite relatively low density values, it has been shown that film microstructure is of more importance than film density for diffusion barrier application.

Figure 13:
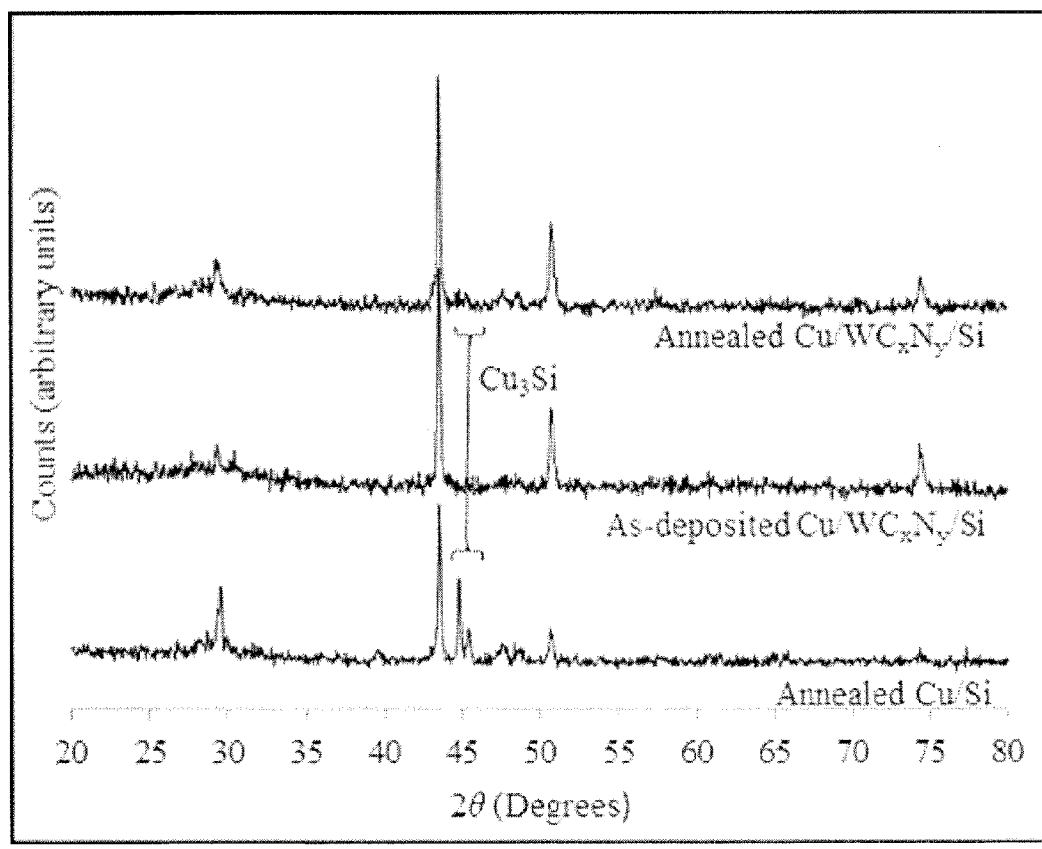
FIG. 13 shows GIXD data taken for a Cu film deposited on a $WN_xC_y$ film, according to an embodiment of the invention, before and after annealing at 500° C., in comparison to a Cu film deposited onto Si without a $WN_xC_y$ film after annealing at 500° C.

$WC_xN_y$ as a Diffusion Barrier:

The integrity of the films as a diffusion barrier was evaluated by depositing approximately 300 nm of Cu onto 30 nm of $WC_xN_y$ film and subjecting the $Cu/WC_xN_y/Si$ stack to thermal stresses. FIG. 13 illustrates the changes in crystallinity between pre- and post-annealed samples. The $Cu_3Si$ that is observed in the annealed Cu/Si control sample is absent in the as-deposited and annealed $Cu/WC_xN_y/Si$ samples.

$WC_xN_y$ from 2

$WC_xN_y$ Film Growth from 2:

Si(100) and Si(111) substrates (Cemat Silicon and Crysteco, respectively) were cut to a size of 1 cm×1 cm, treated for 3 min each in boiling trichloroethylene, boiling acetone and boiling methanol to remove organic contamination from the surface, and subsequently rinsed for 30 sec in boiling deionized water. The substrates were then placed in a buffered-oxide-etch (6:1 $NH_4F$:HF in water) for 2 min to remove the native surface oxide and leave a relatively air-stable hydrogen terminated surface. The samples were blown dry using 99.999% $N_2$, wiped with an acetone soaked lint-free alpha swab, blown dry again, and then placed on a susceptor and loaded into custom designed, vertical cold-wall stagnation-flow aerosol-assisted chemical vapor deposition (AACVD) reactor.

The small area substrates were placed on a pedestal-type graphite susceptor and the reactor volume was evacuated to a base pressure of at least 400 mTorr for approximately 10 min. The system was then purged with 1000 sccm $N_2$ (99.999% purity) at an operating pressure of 350 Torr. The substrate temperature was then increased to ~1000° C. under $H_2$ ambient (99.999% purity) for at least 15 min to reduce a residual $SiO_2$ layer or organic surface contamination. The substrate temperature was then lowered to the desired operating value. A gastight Hamilton syringe (part number 81656) was used to transfer 10 mL of a 0.054 M solution of $WN(NEt_2)_3$ (2) in either pyridine or heptane. A Cole-Parmer syringe pump delivered the precursor solution through 1/16" Tygon tubing to a Cetac nebulizer unit at a rate of 4 mL/hr ($7.47×10^{-5}$ gas-phase precursor mol fraction). The nebulizer system contains a heated piezoelectric quartz plate that vibrates at a rate of 1.44 MHz, which produced the solvent/precursor aerosol. The aerosol mixture was transported to the reaction chamber by 1000 sccm $N_2$ through stainless steel tubing heated to 55° C. Upon runtime completion (nominally 150 min), the samples were removed and characterized.

Diffusion Barrier Tests:

Barrier performance was evaluated by annealing $Cu/WN_xC_y/Si$ stacks from 2 at 500° C. for 30 min under 300 sccm flow of $N_2$ (99.999% from AirGas) at an operating pressure of 3 Torr. $WN_xC_y$ film was grown according to Section II-B, for 27 min at a deposition temperature of 150° C. Samples were then transferred from the deposition chamber to a custom-built Cu MOCVD reactor. This transfer resulted in approximately 5 min post growth exposure to air. Cu metal was grown using $Cu^{I,II}$(hfac)(TMVS) purchased from Gelest Inc. and volatilized in a bubbler system heated to 46° C. The precursor was transported through heated lines (~60° C.) by 50 sccm of $N_2$ to a mixing zone with 300 sccm of $H_2$ (99.999% from AirGas) before entering a reaction chamber heated by a PG/PBN resistive heater (Momentive, Inc.) to 200° C. The mole fraction of each species in the reactor was 0.142, 0.850 and 0.008 for $N_2$, $H_2$ and precursor, respectively.

Subsequent to growth and annealing of Cu (~100 nm)/$WN_xC_y$ (~5.5 nm)/Si stacks, the barrier integrity was evaluated using four-point probe (4PP), XRD, TEM and an SEM etch-pit test. The etch-pit test consisted of dissolving the Cu metal with a dilute nitric acid solution, followed by barrier removal with a $NH_4OH$:$H_2O_2$:$H_2O$ (1:1:4) solution for 10 min. The surface of the resulting sample was then imaged by SEM.

$WN_xC_y$ Film Growth:

AACVD of $WN_xC_y$ from 2 was performed using pyridine and heptane as solvents. Depositions were carried out according to details briefly described in the last section and as previously reported. Films were grown using pyridine as solvent at growth temperature ranging from 100 to 650° C., whereas growth with heptane solutions ranged from 125 to 650° C.

Figure 14:
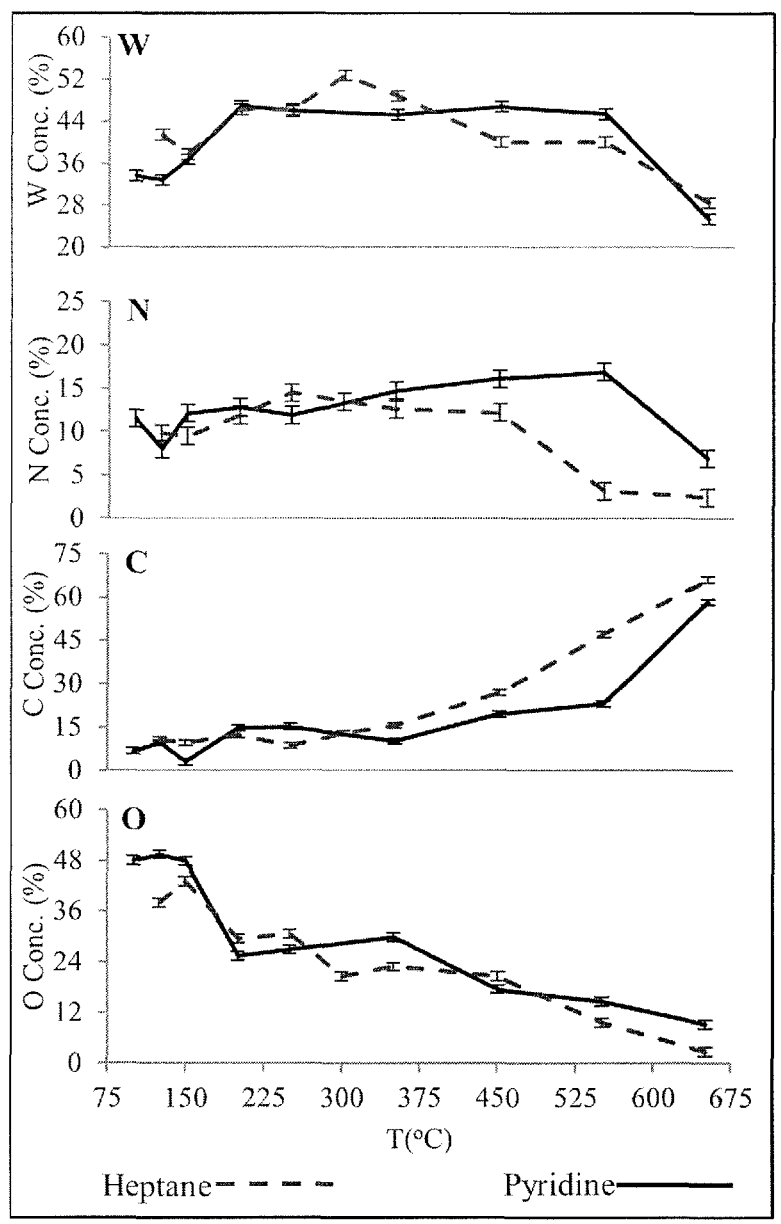
FIG. 14 shows plots of the film compositions for deposition of $WN_xC_y$ from heptane (broken line) and pyridine (solid line) solutions of $WN(NEt_2)_3$ (2) at different deposition temperatures as determined by XPS, according to an embodiment of the invention.
Figure 15:
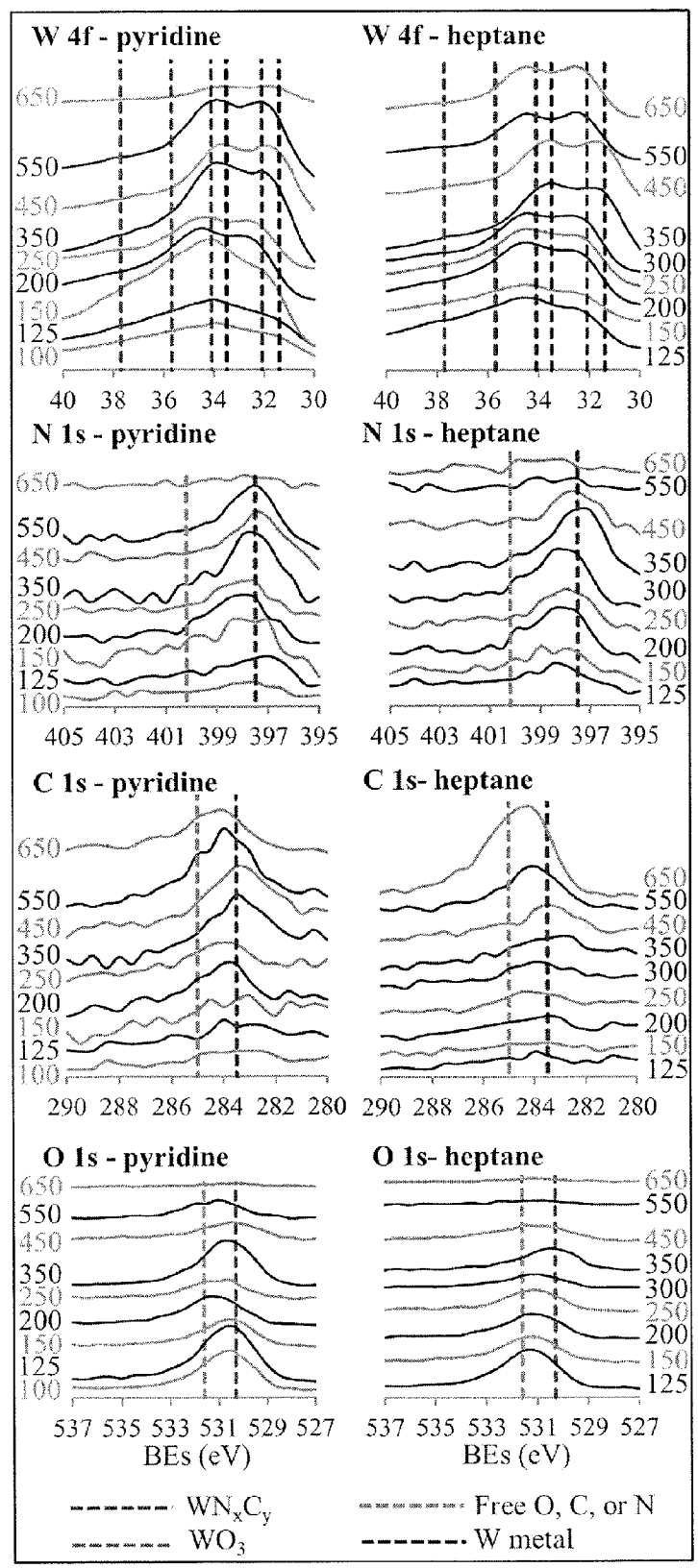
FIG. 15 shows stacked XPS spectra indicating the evolution of the primary elemental peaks with growth temperature for deposition of $WN_xC_y$ from pyridine and heptane solutions of 2 where the superimposed stick patterns are representative of typical binding energy values for associated valence states.

$WN_xC_y$ Film Composition:

XPS was used to quantify atomic composition and analyze elemental valence states of the films deposited from $WN(NEt_2)_3$. FIG. 14 highlights the differences in atomic composition between films deposited from pyridine and heptane solutions. FIG. 15 depicts the evolution of the primary elemental peaks with deposition temperature, where the left column and the right column correspond to deposition from pyridine and heptane solutions, respectively.

Figure 16:
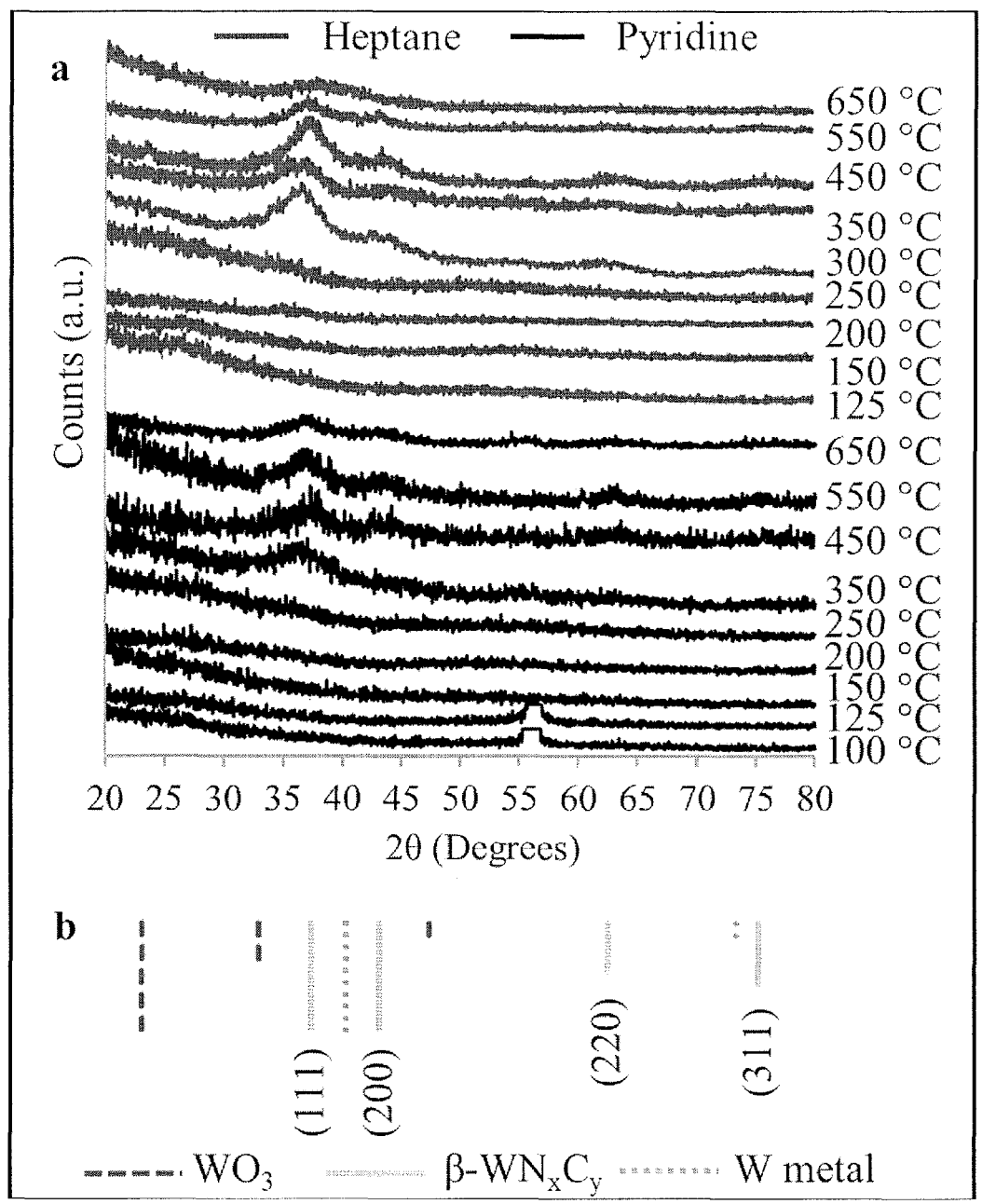
FIG. 16 shows: a) GIXD data taken at various deposition temperatures for $WN_xC_y$ films, according to an embodiment of the invention, grown from pyridine (bottom nine) and heptane (top nine) solutions of 2; and b) accompanying standard XRD diffraction patterns.

$WN_xC_y$ Film Microstructure:

As a diffusion barrier, an amorphous microstructure is preferred over a polycrystalline one because grain boundaries offer low-energy diffusion pathways for Cu migration. FIG. 16a depicts crystal structure data acquired from GIXD measurements, and shows that the resulting material is X-ray amorphous for depositions occurring at temperatures below 300 and 350° C. for heptane and pyridine, respectively.

Figure 17:
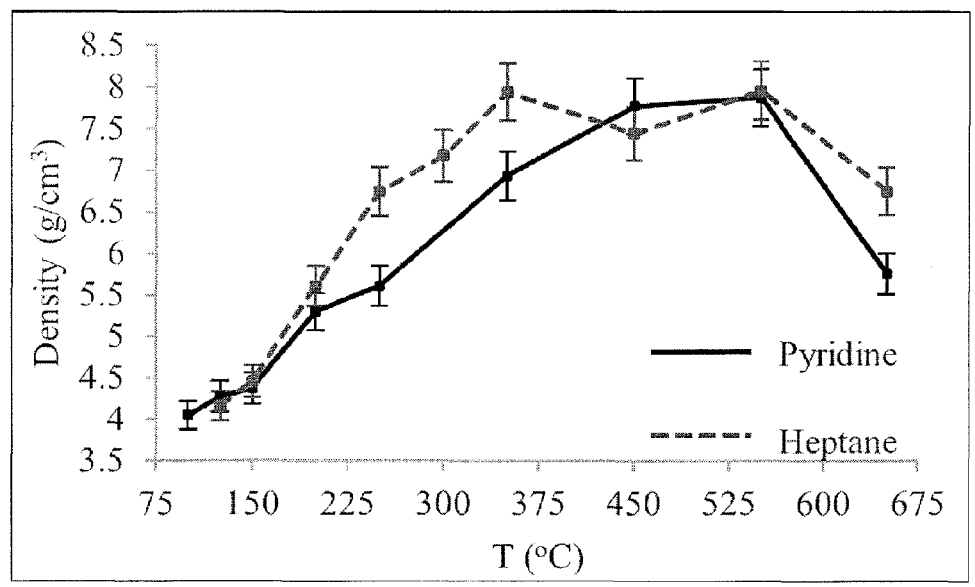
FIG. 17 shows plots of the density for various temperature for deposition of $WN_xC_y$ from pyridine (solid) and heptane (broken) solutions of 2.

$WN_xC_y$ Film Density:

The density of a film and its crystallinity are directly proportional, therefore a balance is required to preserve the amorphous nature of films without sacrificing density. FIG. 17 shows the dependence of density on deposition temperature for films from 2, which clearly shows a densification of films with increasing temperature.

Figure 18:
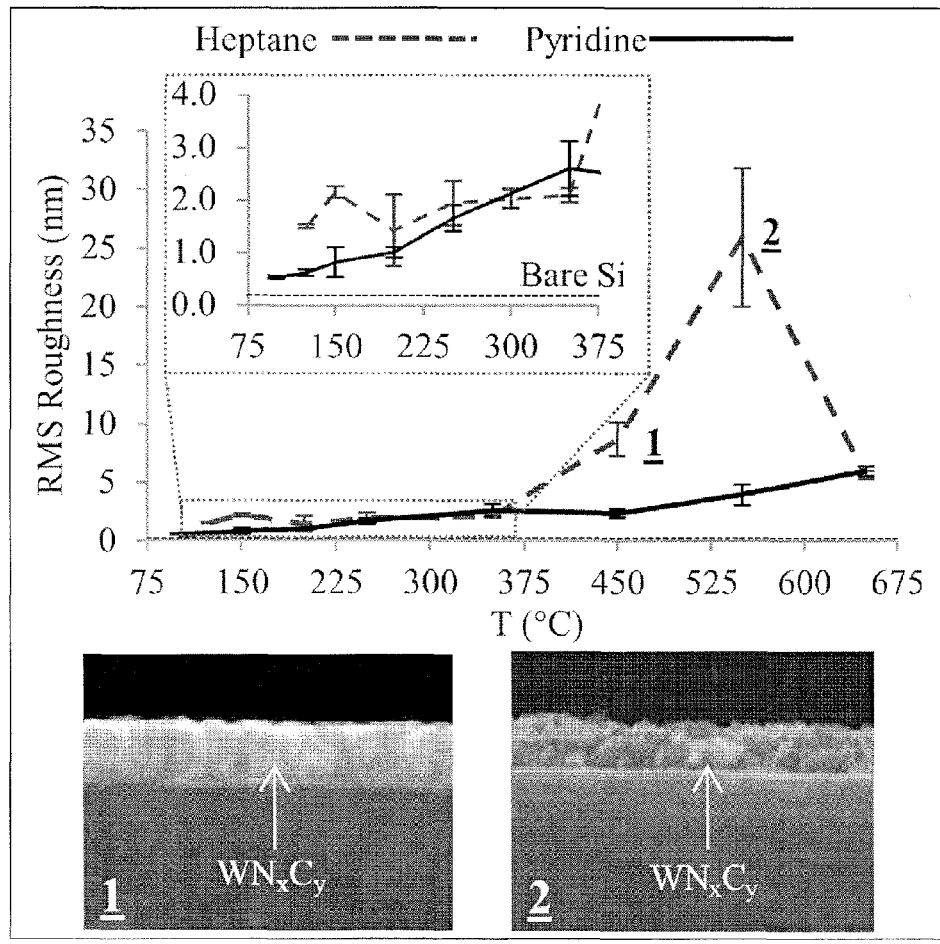
FIG. 18 shows plots of the surface roughness as determined by AFM for films grown by deposition of $WN_xC_y$ from pyridine (solid) and heptane (broken) solutions of 2 at different deposition temperatures where SEM images 1 and 2 are of films grown with heptane and correspond to the points labeled on its curve.

$WN_xC_y$ Film Surface Roughness:

Smooth diffusion barriers promote strong adhesion to neighboring layers and minimize interfacial resistances that can become limiting at ultra-thin dimensions. On average, films from 2 deposited using heptane were rougher than films deposited using pyridine, especially at high temperatures (>350° C.) (FIG. 18). At temperatures below 200° C., films grown with pyridine were highly smooth with a roughness approaching that of the underlying substrate (RMS roughness of 1.8 Å).

Figure 19:
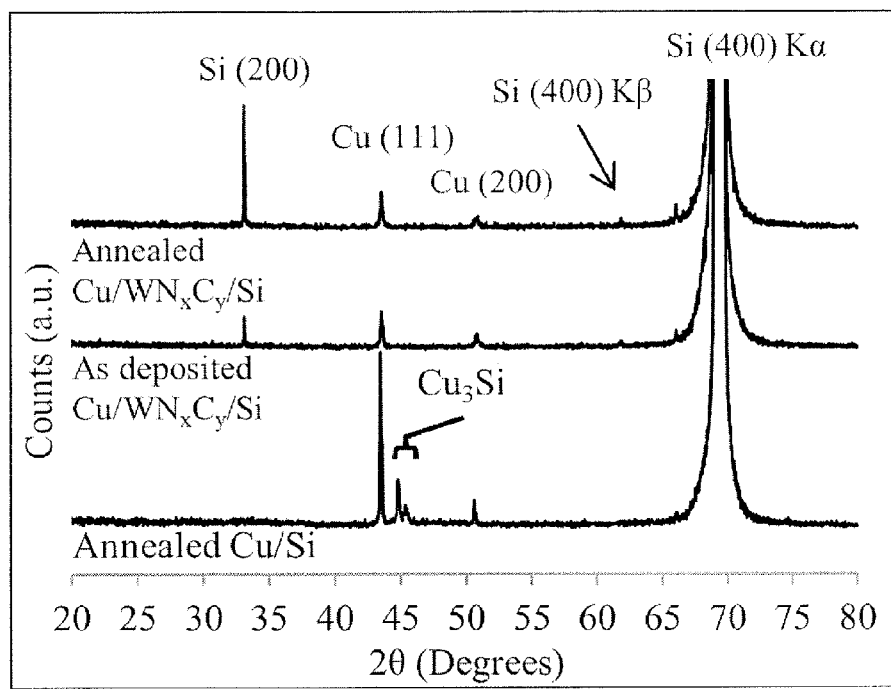
FIG. 19 shows XRD patterns of Cu/Si and Cu/$WN_xC_y$/Si stacks annealed at 500° C. for 30 min and an as-deposited Cu/$WN_xC_y$/Si stack from 2.

Diffusion Barrier Tests:

The integrity of a 5.5 nm thick film of $WN_xC_y$ from 2 was evaluated. FIG. 19 compares XRD spectra of an annealed Cu/Si stack, an as-deposited Cu (~100 nm)/$WN_xC_y$ (~5.5 nm)/Si stack, and an annealed Cu (~100 nm)/$WN_xC_y$ (~5.5 nm)/Si stack. There are two Cu peaks positioned at 43.51 °2θ and 50.83 °2θ corresponding to Cu (111) and Cu (200) planes, whereas the peaks located at 44.79 °2θ and 45.35 °2θ are attributed to $Cu_3Si$ (110) and $Cu_3Si$ (103) planes, respectively. $Cu_3Si$ peaks are not observed in either the annealed or as-deposited Cu/$WN_xC_y$/Si stacks, which is additional evidence of effective barrier performance.

Figure 20:
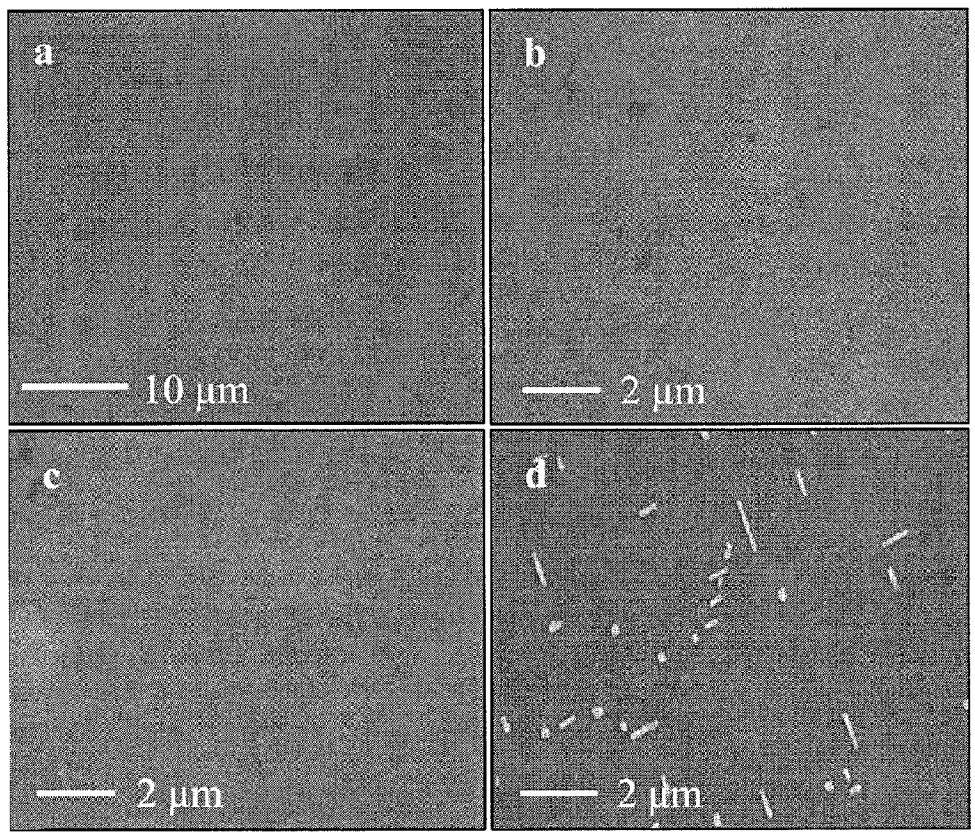
FIG. 20 shows EM images of an etch-pit test for: a) annealed Cu/$WN_xC_y$/Si stack; b) annealed Cu/$WN_xC_y$/Si stack; c) as deposited Cu/$WN_xC_y$/Si stack; and d) a failed barrier for comparison where bright rectangles are $Cu_3Si$ precipitates.
Figure 21:
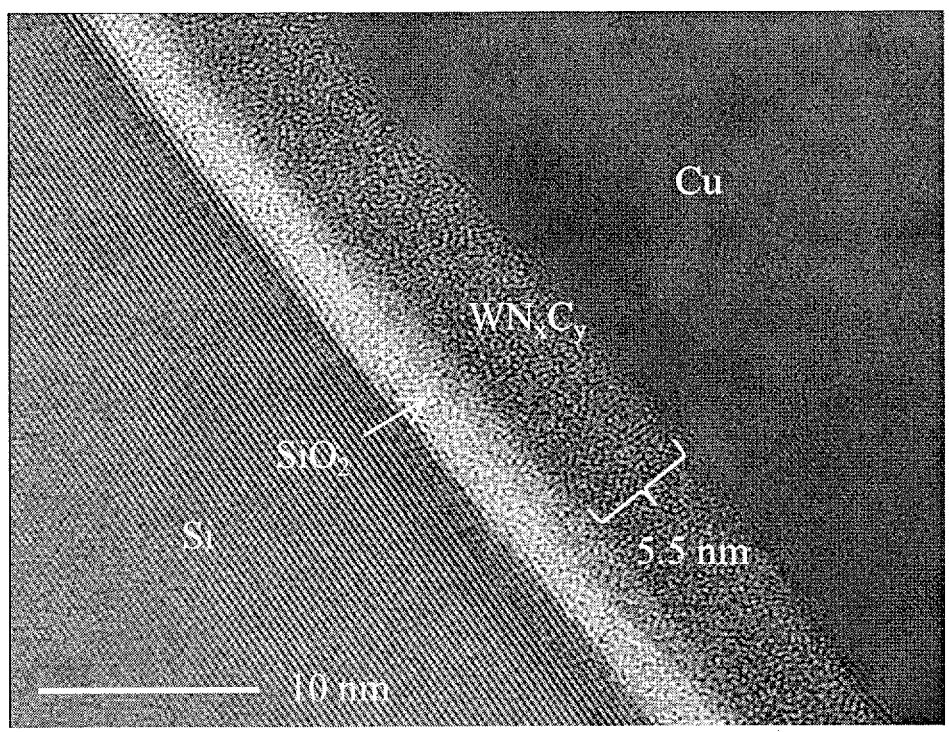
FIG. 21 shows a TEM image of an annealed Cu/$WN_xC_y$/Si stack from 2, according to an embodiment of the invention.

The SEM etch-pit test is more sensitive to Cu diffusion and is used to evaluate small-scale diffusion over a large area, while TEM imaging is used to determine the integrity of the interfaces. In etch-pit testing, the Cu and $WN_xC_y$ layers are chemically removed to expose the bare substrate, which is subsequently imaged by SEM, as shown in FIG. 20. If the barrier had failed, $Cu_3Si$ precipitates would appear as micrometer-sized bright rectangles as in FIG. 20d. The absence of these precipitates after annealing, where the images FIGS. 20a-c confirm the effectiveness of the barrier. A final review of the barrier integrity was conducted using TEM as shown in FIG. 21. The image shows the intact and defined interfaces of the Cu (~100 nm)/$WN_xC_y$ (~5.5 nm)/Si stack. An unintended native $SiO_2$ layer is present between the Si and $WN_xC_y$.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A $WN_x$ or $WN_xC_y$ precursor, comprising a tungsten nitrido complex of formula:

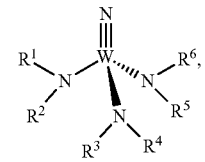

wherein: $R^1$, $R^2$, $R^3$, $R^4$, $R^5$, and $R^6$ are independently H, $C_1$-$C_8$ alkyl, $C_1$-$C_8$ perfluoroalkyl, $C_1$-$C_8$ fluorohydroalkyl, or $SiR^{16}R^{17}R^{18}$; wherein $R^{16}$, $R^{17}$ and $R^{18}$ are independently H, $C_1$-$C_8$ alkyl, aryl, $C_1$-$C_8$ perfluoroalkyl, or $C_1$-$C_8$ fluorohydroalkyl; and wherein at least one of $R^1$, $R^2$, $R^3$, $R^4$, $R^5$, or $R^6$ is not methyl.

2. A method of preparing a tungsten nitrido complex of the structure

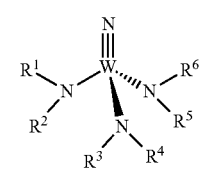

comprising:
providing $WCl_6$;
mixing $WCl_6$ with trimethylsilyl azide to form $[WNCl_3]_4 \cdot 1.1DCE$ (DCE=1,2-dichloroethane);
combining the $[WNCl_3]_4 \cdot 1.1DCE$ with tert-butanol and a stoichiometric quantity of sodium tert-butoxide to form $WN(O^tBu)_3$; and
combining the $WN(O^tBu)_3$ with one or more compounds of the formula $Zr(NR_aR_b)_4$ to form (I), wherein: $R^1$, $R^2$, $R^3$, $R^4$, $R^5$, $R^6$, are independently $R_a$ or $R_b$, wherein $R_a$ or $R_b$ are independently H, $C_1$-$C_8$ alkyl, $C_1$-$C_8$ perfluoroalkyl, $C_1$-$C_8$ fluorohydroalkyl, or $SiR^{16}R^{17}R^{18}$; wherein $R^{16}$, $R^{17}$ and $R^{18}$ are independently H, $C_1$-$C_8$ alkyl, aryl, $C_1$-$C_8$ perfluoroalkyl, or $C_1$-$C_8$ fluorohydroalkyl.

3. A method of preparing a tungsten nitrido complex of the structure

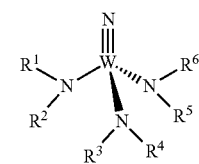

comprising:
providing $WN(N(CH_3)_2)_3$;
combining the $WN(N(CH_3)_2)_3$ with at least one amine of the formula $NHR_aR_b$, wherein: $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are independently $R_a$ or $R_b$, wherein $R_a$ or $R_b$ are independently H, $C_1$-$C_8$ alkyl, $C_1$-$C_8$ perfluoroalkyl, $C_1$-$C_8$ fluorohydroalkyl, or $SiR^{16}R^{17}R^{18}$; wherein $R^{16}$, $R^{17}$ and $R^{18}$ are independently H, $C_1$-$C_8$ alkyl, aryl, $C_1$-$C_8$ perfluoroalkyl, or $C_1$-$C_8$ fluorohydroalkyl, and wherein the amine of the formula $NHR_aR_b$ is less volatile than $NH(CH_3)_2$; and removing $NH(CH_3)_2$ as a volatile.

4. The $WN_x$ or $WN_xC_y$ precursor, according to claim 1, wherein $R^1$, $R^2$, $R^3$, $R^4$, $R^5$, and $R^6$ are ethyl or propyl.

5. The $WN_x$ or $WN_xC_y$ precursor, according to claim 1, wherein $R^1$, $R^3$, and $R^5$ are methyl and $R^2$, $R^4$, and $R^6$ are ethyl or propyl.

6. The $WN_x$ or $WN_xC_y$ precursor, according to claim 1, wherein $R^1$, $R^3$, and $R^5$ are ethyl and $R^2$, $R^4$, and $R^6$ are propyl.

\* \* \* \* \*

UNITED STATES PATENT AND TRADEMARK OFFICE
CERTIFICATE OF CORRECTION

| | | |
|---|---|---|
| PATENT NO. | : 9,540,284 B2 | Page 1 of 1 |
| APPLICATION NO. | : 14/575026 | |
| DATED | : January 10, 2017 | |
| INVENTOR(S) | : Lisa McElwee-White et al. | |

It is certified that error appears in the above-identified patent and that said Letters Patent is hereby corrected as shown below:

In the Specification

Column 7,
Line 57, "benzene-$ds_8$ and" should read --benzene-$d_8$ and--.

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*